US012763187B2

(12) United States Patent
Lee et al.

(10) Patent No.: US 12,763,187 B2
(45) Date of Patent: Oct. 13, 2026

(54) SYSTEMS AND METHODS FOR ENSURING SUFFICIENT BOLUS DOSING FOR MEAL COMPENSATION

(71) Applicant: INSULET CORPORATION, Acton, MA (US)

(72) Inventors: Joon Bok Lee, Acton, MA (US); Rangarajan Narayanaswami, Weston, MA (US); Yibin Zheng, Hartland, WI (US); Ashutosh Zade, San Diego, CA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 893 days.

(21) Appl. No.: 18/155,215

(22) Filed: Jan. 17, 2023

(65) Prior Publication Data

US 2023/0230668 A1 Jul. 20, 2023

Related U.S. Application Data

(60) Provisional application No. 63/300,460, filed on Jan. 18, 2022.

(51) Int. Cl.
*G16H 20/17* (2018.01)
*A61M 5/142* (2006.01)
*A61M 5/172* (2006.01)

(52) U.S. Cl.
CPC ............ *G16H 20/17* (2018.01); *A61M 5/142* (2013.01); *A61M 5/1723* (2013.01); (Continued)

(58) Field of Classification Search
None
See application file for complete search history.

(56) References Cited

U.S. PATENT DOCUMENTS 303,013 A 8/1884 Horton
445,545 A 2/1891 Crane
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Goodwin Procter LLP

(57) ABSTRACT

Disclosed herein are systems and methods for providing safeguards, in an automatic drug delivery system, to prevent or compensate for insufficient delivery of bolus doses of a liquid drug. The safeguards include, for example, features built into the medication delivery algorithm to allow the medication delivery algorithm to ensure that proper bolus doses are delivered, either manually by the user or automatically by the drug delivery system. In addition, various methods are described for providing the medication delivery algorithm with a means for determining when a meal has been ingested and, in some embodiments, for providing an automatic bolus dose of the liquid drug in response to the determination.

20 Claims, 10 Drawing Sheets

(52) U.S. Cl.
CPC ............ *A61M 2005/14208* (2013.01); *A61M 2205/52* (2013.01); *A61M 2230/201* (2013.01)

(56) References Cited

U.S. PATENT DOCUMENTS

| | | | |
|---|---|---|---|
| 588,583 | A | 8/1897 | Lade |
| 1,441,508 | A | 1/1923 | Jensen |
| 2,283,925 | A | 5/1942 | Harvey |
| 2,797,149 | A | 6/1957 | Skeggs |
| 2,886,529 | A | 5/1959 | Guillaud |
| 3,574,114 | A | 4/1971 | Monforte |
| 3,614,554 | A | 10/1971 | Shield |
| 3,631,847 | A | 1/1972 | Hobbs |
| 3,634,039 | A | 1/1972 | Brondy |
| 3,812,843 | A | 5/1974 | Wootten et al. |
| 3,841,328 | A | 10/1974 | Jensen |
| 3,885,662 | A | 5/1975 | Schaefer |
| 3,963,380 | A | 6/1976 | Thomas, Jr. et al. |
| 3,983,077 | A | 9/1976 | Fuller et al. |
| 4,055,175 | A | 10/1977 | Clemens et al. |
| 4,108,177 | A | 8/1978 | Pistor |
| 4,146,029 | A | 3/1979 | Ellinwood, Jr. |
| 4,151,845 | A | 5/1979 | Clemens |
| 4,245,634 | A | 1/1981 | Albisser et al. |
| 4,268,150 | A | 5/1981 | Chen |
| 4,313,439 | A | 2/1982 | Babb et al. |
| 4,368,980 | A | 1/1983 | Aldred et al. |
| 4,373,527 | A | 2/1983 | Fischell |
| 4,400,683 | A | 8/1983 | Eda et al. |
| 4,403,984 | A | 9/1983 | Ash et al. |
| 4,424,720 | A | 1/1984 | Bucchianeri |
| 4,435,173 | A | 3/1984 | Siposs et al. |
| 4,464,170 | A | 8/1984 | Clemens et al. |
| 4,469,481 | A | 9/1984 | Kobayashi |
| 4,475,901 | A | 10/1984 | Kraegen et al. |
| 4,498,843 | A | 2/1985 | Schneider et al. |
| 4,507,115 | A | 3/1985 | Kambara et al. |
| 4,523,170 | A | 6/1985 | Huth, III |
| 4,526,568 | A | 7/1985 | Clemens et al. |
| 4,526,569 | A | 7/1985 | Bernardi |
| 4,529,401 | A | 7/1985 | Leslie et al. |
| 4,551,134 | A | 11/1985 | Slavik et al. |
| 4,559,033 | A | 12/1985 | Stephen et al. |
| 4,559,037 | A | 12/1985 | Franetzki et al. |
| 4,562,751 | A | 1/1986 | Nason et al. |
| 4,573,968 | A | 3/1986 | Parker |
| 4,585,439 | A | 4/1986 | Michel |
| 4,601,707 | A | 7/1986 | Albisser et al. |
| 4,624,661 | A | 11/1986 | Arimond |
| 4,633,878 | A | 1/1987 | Bombardieri |
| 4,634,427 | A | 1/1987 | Hannula et al. |
| 4,646,038 | A | 2/1987 | Wanat |
| 4,657,529 | A | 4/1987 | Prince et al. |
| 4,678,408 | A | 7/1987 | Nason et al. |
| 4,684,368 | A | 8/1987 | Kenyon |
| 4,685,903 | A | 8/1987 | Cable et al. |
| 4,731,726 | A | 3/1988 | Allen, III |
| 4,743,243 | A | 5/1988 | Vaillancourt |
| 4,755,169 | A | 7/1988 | Sarnoff et al. |
| 4,755,173 | A | 7/1988 | Konopka et al. |
| 4,759,120 | A | 7/1988 | Bernstein |
| 4,781,688 | A | 11/1988 | Thoma et al. |
| 4,781,693 | A | 11/1988 | Martinez et al. |
| 4,808,161 | A | 2/1989 | Kamen |
| 4,854,170 | A | 8/1989 | Brimhall et al. |
| 4,859,492 | A | 8/1989 | Rogers, Jr. et al. |
| 4,880,770 | A | 11/1989 | Mir et al. |
| 4,886,499 | A | 12/1989 | Cirelli et al. |
| 4,898,578 | A | 2/1990 | Rubalcaba, Jr. |
| 4,898,579 | A | 2/1990 | Groshong et al. |
| 4,900,292 | A | 2/1990 | Berry et al. |
| 4,919,596 | A | 4/1990 | Slate et al. |
| 4,925,444 | A | 5/1990 | Orkin et al. |
| 4,940,527 | A | 7/1990 | Kazlauskas et al. |
| 4,944,659 | A | 7/1990 | Labbe et al. |
| 4,967,201 | A | 10/1990 | Rich, III |
| 4,969,874 | A | 11/1990 | Michel et al. |
| 4,975,581 | A | 12/1990 | Robinson et al. |
| 4,976,720 | A | 12/1990 | Machold et al. |
| 4,981,140 | A | 1/1991 | Wyatt |
| 4,994,047 | A | 2/1991 | Walker et al. |
| 5,007,286 | A | 4/1991 | Malcolm et al. |
| 5,007,458 | A | 4/1991 | Marcus et al. |
| 5,062,841 | A | 11/1991 | Siegel |
| 5,084,749 | A | 1/1992 | Losee et al. |
| 5,097,834 | A | 3/1992 | Skrabal |
| 5,102,406 | A | 4/1992 | Arnold |
| 5,109,850 | A | 5/1992 | Blanco et al. |
| 5,125,415 | A | 6/1992 | Bell |
| 5,130,675 | A | 7/1992 | Sugawara |
| 5,134,079 | A | 7/1992 | Cusack et al. |
| 5,139,999 | A | 8/1992 | Gordon et al. |
| 5,153,827 | A | 10/1992 | Coutre et al. |
| 5,154,973 | A | 10/1992 | Imagawa et al. |
| 5,165,406 | A | 11/1992 | Wong |
| 5,176,662 | A | 1/1993 | Bartholomew et al. |
| 5,178,609 | A | 1/1993 | Ishikawa |
| 5,189,609 | A | 2/1993 | Tivig et al. |
| 5,198,824 | A | 3/1993 | Poradish |
| 5,205,819 | A | 4/1993 | Ross et al. |
| 5,207,642 | A | 5/1993 | Orkin et al. |
| 5,213,483 | A | 5/1993 | Flaherty et al. |
| 5,217,754 | A | 6/1993 | Santiago-Aviles et al. |
| 5,219,377 | A | 6/1993 | Poradish |
| 5,232,439 | A | 8/1993 | Campbell et al. |
| 5,237,993 | A | 8/1993 | Skrabal |
| 5,244,463 | A | 9/1993 | Cordner, Jr. et al. |
| 5,254,096 | A | 10/1993 | Rondelet et al. |
| 5,257,980 | A | 11/1993 | Van Antwerp et al. |
| 5,261,882 | A | 11/1993 | Sealfon |
| 5,263,198 | A | 11/1993 | Geddes et al. |
| 5,272,485 | A | 12/1993 | Mason et al. |
| 5,273,517 | A | 12/1993 | Barone et al. |
| 5,281,202 | A | 1/1994 | Weber et al. |
| 5,281,808 | A | 1/1994 | Kunkel |
| 5,299,571 | A | 4/1994 | Mastrototaro |
| 5,308,982 | A | 5/1994 | Ivaldi et al. |
| 5,342,298 | A | 8/1994 | Michaels et al. |
| 5,346,476 | A | 9/1994 | Elson |
| 5,364,342 | A | 11/1994 | Beuchat et al. |
| 5,377,674 | A | 1/1995 | Kuestner |
| 5,380,665 | A | 1/1995 | Cusack et al. |
| 5,385,539 | A | 1/1995 | Maynard |
| 5,389,078 | A | 2/1995 | Zalesky |
| 5,403,797 | A | 4/1995 | Ohtani et al. |
| 5,411,889 | A | 5/1995 | Hoots et al. |
| 5,421,812 | A | 6/1995 | Langley et al. |
| 5,427,988 | A | 6/1995 | Sengupta et al. |
| 5,433,710 | A | 7/1995 | VanAntwerp et al. |
| 5,456,945 | A | 10/1995 | McMillan et al. |
| 5,468,727 | A | 11/1995 | Phillips et al. |
| 5,478,610 | A | 12/1995 | Desu et al. |
| 5,505,709 | A | 4/1996 | Funderburk et al. |
| 5,505,828 | A | 4/1996 | Wong et al. |
| 5,507,288 | A | 4/1996 | Bocker et al. |
| 5,513,382 | A | 4/1996 | Agahi-Kesheh et al. |
| 5,533,389 | A | 7/1996 | Kamen et al. |
| 5,535,445 | A | 7/1996 | Gunton |
| 5,540,772 | A | 7/1996 | McMillan et al. |
| 5,543,773 | A | 8/1996 | Evans et al. |
| 5,558,640 | A | 9/1996 | Pfeiler et al. |
| 5,569,186 | A | 10/1996 | Lord et al. |
| 5,582,593 | A | 12/1996 | Hultman |
| 5,584,053 | A | 12/1996 | Kommrusch et al. |
| 5,584,813 | A | 12/1996 | Livingston et al. |
| 5,590,387 | A | 12/1996 | Schmidt et al. |
| 5,609,572 | A | 3/1997 | Lang |
| 5,614,252 | A | 3/1997 | McMillan et al. |
| 5,625,365 | A | 4/1997 | Tom et al. |
| 5,635,433 | A | 6/1997 | Sengupta |
| 5,637,095 | A | 6/1997 | Nason et al. |
| 5,665,065 | A | 9/1997 | Colman et al. |
| 5,665,070 | A | 9/1997 | McPhee |
| 5,678,539 | A | 10/1997 | Schubert et al. |

(56) References Cited

U.S. PATENT DOCUMENTS

| | | | |
|---|---|---|---|
| 5,685,844 | A | 11/1997 | Marttila |
| 5,685,859 | A | 11/1997 | Kornerup |
| 5,693,018 | A | 12/1997 | Kriesel et al. |
| 5,697,899 | A | 12/1997 | Hillman et al. |
| 5,700,695 | A | 12/1997 | Yassinzadeh et al. |
| 5,703,364 | A | 12/1997 | Rosenthal |
| 5,707,459 | A | 1/1998 | Itoyama et al. |
| 5,707,715 | A | 1/1998 | deRochemont et al. |
| 5,713,875 | A | 2/1998 | Tanner, II |
| 5,714,123 | A | 2/1998 | Sohrab |
| 5,716,343 | A | 2/1998 | Kriesel et al. |
| 5,722,397 | A | 3/1998 | Eppstein |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | McMillan et al. |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | McPhee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,817,007 | A | 10/1998 | Fodgaard et al. |
| 5,820,622 | A | 10/1998 | Gross et al. |
| 5,823,951 | A | 10/1998 | Messerschmidt |
| 5,839,467 | A | 11/1998 | Saaski et al. |
| 5,840,020 | A | 11/1998 | Heinonen et al. |
| 5,848,991 | A | 12/1998 | Gross et al. |
| 5,851,197 | A | 12/1998 | Marano et al. |
| 5,854,608 | A | 12/1998 | Leisten |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | McWha |
| 5,879,310 | A | 3/1999 | Sopp et al. |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | McPhee |
| 5,911,716 | A | 6/1999 | Rake et al. |
| 5,919,167 | A | 7/1999 | Mulhauser et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,957,890 | A | 9/1999 | Mann et al. |
| 5,961,492 | A | 10/1999 | Kriesel et al. |
| 5,965,848 | A | 10/1999 | Altschul et al. |
| 5,971,941 | A | 10/1999 | Simons et al. |
| 5,993,423 | A | 11/1999 | Choi |
| 5,997,501 | A | 12/1999 | Gross et al. |
| 6,017,318 | A | 1/2000 | Gauthier et al. |
| 6,019,747 | A | 2/2000 | McPhee |
| 6,023,251 | A | 2/2000 | Koo et al. |
| 6,024,539 | A | 2/2000 | Blomquist |
| 6,027,826 | A | 2/2000 | deRochemont et al. |
| 6,028,568 | A | 2/2000 | Asakura et al. |
| 6,031,445 | A | 2/2000 | Marty et al. |
| 6,032,059 | A | 2/2000 | Henning et al. |
| 6,036,924 | A | 3/2000 | Simons et al. |
| 6,040,578 | A | 3/2000 | Malin et al. |
| 6,040,805 | A | 3/2000 | Huynh et al. |
| 6,046,707 | A | 4/2000 | Gaughan et al. |
| 6,049,727 | A | 4/2000 | Crothall |
| 6,050,978 | A | 4/2000 | Orr et al. |
| 6,052,040 | A | 4/2000 | Hino |
| 6,058,934 | A | 5/2000 | Sullivan |
| 6,066,103 | A | 5/2000 | Duchon et al. |
| 6,071,292 | A | 6/2000 | Makower et al. |
| 6,072,180 | A | 6/2000 | Kramer et al. |
| 6,077,055 | A | 6/2000 | Vilks |
| 6,090,092 | A | 7/2000 | Fowles et al. |
| 6,101,406 | A | 8/2000 | Hacker et al. |
| 6,102,872 | A | 8/2000 | Doneen et al. |
| 6,111,544 | A | 8/2000 | Dakeya et al. |
| 6,115,673 | A | 9/2000 | Malin et al. |
| 6,123,827 | A | 9/2000 | Wong et al. |
| 6,124,134 | A | 9/2000 | Stark |
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,143,432 | A | 11/2000 | de Rochemont et al. |
| 6,154,176 | A | 11/2000 | Fathy et al. |
| 6,157,041 | A | 12/2000 | Thomas et al. |
| 6,161,028 | A | 12/2000 | Braig et al. |
| 6,162,639 | A | 12/2000 | Douglas |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,196,046 | B1 | 3/2001 | Braig et al. |
| 6,200,287 | B1 | 3/2001 | Keller et al. |
| 6,200,293 | B1 | 3/2001 | Kriesel et al. |
| 6,200,338 | B1 | 3/2001 | Solomon et al. |
| 6,204,203 | B1 | 3/2001 | Narwankar et al. |
| 6,208,843 | B1 | 3/2001 | Huang et al. |
| 6,214,629 | B1 | 4/2001 | Freitag et al. |
| 6,222,489 | B1 | 4/2001 | Tsuru et al. |
| 6,226,082 | B1 | 5/2001 | Roe |
| 6,244,776 | B1 | 6/2001 | Wiley |
| 6,261,065 | B1 | 7/2001 | Nayak et al. |
| 6,262,798 | B1 | 7/2001 | Shepherd et al. |
| 6,266,020 | B1 | 7/2001 | Chang |
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kunstner |
| 6,300,894 | B1 | 10/2001 | Lynch et al. |
| 6,309,370 | B1 | 10/2001 | Haim et al. |
| 6,312,888 | B1 | 11/2001 | Wong et al. |
| 6,320,547 | B1 | 11/2001 | Fathy et al. |
| 6,323,549 | B1 | 11/2001 | deRochemont et al. |
| 6,334,851 | B1 | 1/2002 | Hayes et al. |
| 6,363,609 | B1 | 4/2002 | Pickren |
| 6,375,627 | B1 | 4/2002 | Mauze et al. |
| 6,375,638 | B2 | 4/2002 | Nason et al. |
| 6,379,301 | B1 | 4/2002 | Worthington et al. |
| 6,402,689 | B1 | 6/2002 | Scarantino et al. |
| 6,470,279 | B1 | 10/2002 | Samsoondar |
| 6,474,219 | B2 | 11/2002 | Klitmose et al. |
| 6,475,196 | B1 | 11/2002 | Vachon |
| 6,477,065 | B2 | 11/2002 | Parks |
| 6,477,901 | B1 | 11/2002 | Tadigadapa et al. |
| 6,484,044 | B1 | 11/2002 | Lilienfeld-Toal |
| 6,485,461 | B1 | 11/2002 | Mason et al. |
| 6,485,462 | B1 | 11/2002 | Kriesel |
| 6,491,656 | B1 | 12/2002 | Morris |
| 6,492,949 | B1 | 12/2002 | Breglia et al. |
| 6,496,149 | B1 | 12/2002 | Birnbaum et al. |
| 6,501,415 | B1 | 12/2002 | Viana et al. |
| 6,512,937 | B2 | 1/2003 | Blank et al. |
| 6,520,936 | B1 | 2/2003 | Mann |
| 6,525,509 | B1 | 2/2003 | Petersson et al. |
| 6,527,744 | B1 | 3/2003 | Kriesel et al. |
| 6,528,809 | B1 | 3/2003 | Thomas et al. |

(56) References Cited

U.S. PATENT DOCUMENTS

| | | | |
|---|---|---|---|
| 6,537,249 | B2 | 3/2003 | Kriesell et al. |
| 6,540,260 | B1 | 4/2003 | Tan |
| 6,540,672 | B1 | 4/2003 | Simonsen et al. |
| 6,541,820 | B1 | 4/2003 | Bol |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,552,693 | B1 | 4/2003 | Leisten |
| 6,553,841 | B1 | 4/2003 | Blouch |
| 6,554,798 | B1 | 4/2003 | Mann et al. |
| 6,556,850 | B1 | 4/2003 | Braig et al. |
| 6,558,351 | B1 | 5/2003 | Steil et al. |
| 6,559,735 | B1 | 5/2003 | Hoang et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,562,014 | B2 | 5/2003 | Lin et al. |
| 6,569,115 | B1 | 5/2003 | Barker et al. |
| 6,569,125 | B2 | 5/2003 | Jepson et al. |
| 6,572,542 | B1 | 6/2003 | Houben et al. |
| 6,572,545 | B2 | 6/2003 | Knobbe et al. |
| 6,574,490 | B2 | 6/2003 | Abbink et al. |
| 6,575,905 | B2 | 6/2003 | Knobbe et al. |
| 6,580,934 | B1 | 6/2003 | Braig et al. |
| 6,583,699 | B2 | 6/2003 | Yokoyama |
| 6,595,956 | B1 | 7/2003 | Gross et al. |
| 6,605,151 | B1 | 8/2003 | Wessels et al. |
| 6,611,419 | B1 | 8/2003 | Chakravorty |
| 6,618,603 | B2 | 9/2003 | Varalli et al. |
| 6,620,750 | B2 | 9/2003 | Kim et al. |
| 6,633,772 | B2 | 10/2003 | Ford et al. |
| 6,635,958 | B2 | 10/2003 | Bates et al. |
| 6,639,556 | B2 | 10/2003 | Baba |
| 6,642,908 | B2 | 11/2003 | Pleva et al. |
| 6,645,142 | B2 | 11/2003 | Braig et al. |
| 6,650,303 | B2 | 11/2003 | Kim et al. |
| 6,653,091 | B1 | 11/2003 | Dunn et al. |
| 6,656,158 | B2 | 12/2003 | Mahoney et al. |
| 6,662,030 | B2 | 12/2003 | Khalil et al. |
| 6,669,663 | B1 | 12/2003 | Thompson |
| 6,670,497 | B2 | 12/2003 | Tashino et al. |
| 6,678,542 | B2 | 1/2004 | Braig et al. |
| 6,680,700 | B2 | 1/2004 | Hilgers |
| 6,683,576 | B2 | 1/2004 | Achim |
| 6,686,406 | B2 | 2/2004 | Tomomatsu et al. |
| 6,690,336 | B1 | 2/2004 | Leisten et al. |
| 6,697,605 | B1 | 2/2004 | Atokawa et al. |
| 6,699,218 | B2 | 3/2004 | Flaherty et al. |
| 6,699,221 | B2 | 3/2004 | Vaillancourt |
| 6,718,189 | B2 | 4/2004 | Rohrscheib et al. |
| 6,720,926 | B2 | 4/2004 | Killen et al. |
| 6,721,582 | B2 | 4/2004 | Trepagnier et al. |
| 6,723,072 | B2 | 4/2004 | Flaherty et al. |
| 6,727,785 | B2 | 4/2004 | Killen et al. |
| 6,728,560 | B2 | 4/2004 | Kollias et al. |
| 6,731,244 | B2 | 5/2004 | Killen et al. |
| 6,731,248 | B2 | 5/2004 | Killen et al. |
| 6,733,890 | B2 | 5/2004 | Imanaka et al. |
| 6,740,059 | B2 | 5/2004 | Flaherty |
| 6,740,072 | B2 | 5/2004 | Starkweather et al. |
| 6,741,148 | B2 | 5/2004 | Killen et al. |
| 6,742,249 | B2 | 6/2004 | deRochemont et al. |
| 6,743,744 | B1 | 6/2004 | Kim et al. |
| 6,750,740 | B2 | 6/2004 | Killen et al. |
| 6,750,820 | B2 | 6/2004 | Killen et al. |
| 6,751,490 | B2 | 6/2004 | Esenaliev et al. |
| 6,753,745 | B2 | 6/2004 | Killen et al. |
| 6,753,814 | B2 | 6/2004 | Killen et al. |
| 6,758,835 | B2 | 7/2004 | Close et al. |
| 6,762,237 | B2 | 7/2004 | Glatkowski et al. |
| 6,780,156 | B2 | 8/2004 | Haueter et al. |
| 6,787,181 | B2 | 9/2004 | Uchiyama et al. |
| 6,791,496 | B1 | 9/2004 | Killen et al. |
| 6,810,290 | B2 | 10/2004 | Lebel et al. |
| 6,826,031 | B2 | 11/2004 | Nagai et al. |
| 6,830,623 | B2 | 12/2004 | Hayashi et al. |
| 6,837,858 | B2 | 1/2005 | Cunningham et al. |
| 6,837,988 | B2 | 1/2005 | Leong et al. |
| 6,846,288 | B2 | 1/2005 | Nagar et al. |
| 6,853,288 | B2 | 2/2005 | Ahn et al. |
| 6,858,892 | B2 | 2/2005 | Yamagata |
| 6,862,534 | B2 | 3/2005 | Sterling et al. |
| 6,864,848 | B2 | 3/2005 | Sievenpiper |
| 6,865,408 | B1 | 3/2005 | Abbink et al. |
| 6,871,396 | B2 | 3/2005 | Sugaya et al. |
| 6,878,871 | B2 | 4/2005 | Scher et al. |
| 6,883,778 | B1 | 4/2005 | Newton et al. |
| 6,890,291 | B2 | 5/2005 | Robinson et al. |
| 6,905,989 | B2 | 6/2005 | Ellis et al. |
| 6,906,674 | B2 | 6/2005 | McKinzie, III et al. |
| 6,914,566 | B2 | 7/2005 | Beard |
| 6,919,119 | B2 | 7/2005 | Kalkan et al. |
| 6,928,298 | B2 | 8/2005 | Furutani et al. |
| 6,936,029 | B2 | 8/2005 | Mann et al. |
| 6,943,430 | B2 | 9/2005 | Kwon |
| 6,943,731 | B2 | 9/2005 | Killen et al. |
| 6,949,081 | B1 | 9/2005 | Chance |
| 6,958,809 | B2 | 10/2005 | Sterling et al. |
| 6,963,259 | B2 | 11/2005 | Killen et al. |
| 6,989,891 | B2 | 1/2006 | Braig et al. |
| 6,990,366 | B2 | 1/2006 | Say et al. |
| 7,002,436 | B2 | 2/2006 | Ma et al. |
| 7,008,404 | B2 | 3/2006 | Nakajima |
| 7,009,180 | B2 | 3/2006 | Sterling et al. |
| 7,016,713 | B2 | 3/2006 | Gardner et al. |
| 7,018,360 | B2 | 3/2006 | Flaherty et al. |
| 7,025,743 | B2 | 4/2006 | Mann et al. |
| 7,025,744 | B2 | 4/2006 | Utterberg et al. |
| 7,027,848 | B2 | 4/2006 | Robinson et al. |
| 7,043,288 | B2 | 5/2006 | Davis, III et al. |
| 7,047,637 | B2 | 5/2006 | deRochemont et al. |
| 7,060,059 | B2 | 6/2006 | Keith et al. |
| 7,060,350 | B2 | 6/2006 | Takaya et al. |
| 7,061,593 | B2 | 6/2006 | Braig et al. |
| 7,096,124 | B2 | 8/2006 | Sterling et al. |
| 7,115,205 | B2 | 10/2006 | Robinson et al. |
| 7,116,949 | B2 | 10/2006 | Irie et al. |
| 7,128,727 | B2 | 10/2006 | Flaherty et al. |
| 7,137,694 | B2 | 11/2006 | Ferran et al. |
| 7,139,593 | B2 | 11/2006 | Kavak et al. |
| 7,139,598 | B2 | 11/2006 | Hull et al. |
| 7,144,384 | B2 | 12/2006 | Gorman et al. |
| 7,160,272 | B1 | 1/2007 | Eyal et al. |
| 7,171,252 | B1 | 1/2007 | Scarantino et al. |
| 7,190,988 | B2 | 3/2007 | Say et al. |
| 7,204,823 | B2 | 4/2007 | Estes et al. |
| 7,230,316 | B2 | 6/2007 | Yamazaki et al. |
| 7,248,912 | B2 | 7/2007 | Gough et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,291,782 | B2 | 11/2007 | Sager et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 | 7/2008 | Ginsberg |
| 7,405,698 | B2 | 7/2008 | de Rochemont |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 | 2/2009 | Van Den Berghe et al. |
| 7,500,949 | B2 | 3/2009 | Gottlieb et al. |
| 7,509,156 | B2 | 3/2009 | Flanders |
| 7,522,124 | B2 | 4/2009 | Smith et al. |
| 7,547,281 | B2 | 6/2009 | Hayes et al. |
| 7,553,512 | B2 | 6/2009 | Kodas et al. |
| 7,564,887 | B2 | 7/2009 | Wang et al. |
| 7,569,030 | B2 | 8/2009 | Lebel et al. |
| 7,595,623 | B2 | 9/2009 | Bennett |

(56) References Cited

U.S. PATENT DOCUMENTS 7,608,042 B2 10/2009 Goldberger et al.
7,651,845 B2 1/2010 Doyle, III et al.
7,652,901 B2 1/2010 Kirchmeier et al.
7,680,529 B2 3/2010 Kroll
7,714,794 B2 5/2010 Tavassoli Hozouri
7,734,323 B2 6/2010 Blomquist et al.
7,763,917 B2 7/2010 de Rochemont
7,766,829 B2 8/2010 Sloan et al.
7,771,391 B2 8/2010 Carter
7,785,258 B2 8/2010 Braig et al.
7,785,313 B2 * 8/2010 Mastrototaro ....... A61B 5/1495 604/503
7,806,854 B2 10/2010 Damiano et al.
7,806,886 B2 10/2010 Kanderian, Jr. et al.
7,812,774 B2 10/2010 Friman et al.
7,918,825 B2 4/2011 OConnor et al.
7,946,985 B2 5/2011 Mastrototaro et al.
7,972,296 B2 7/2011 Braig et al.
8,066,805 B2 11/2011 Zurcher et al.
8,069,690 B2 12/2011 DeSantolo et al.
8,114,489 B2 2/2012 Nemat-Nasser et al.
8,140,275 B2 * 3/2012 Campbell ......... A61M 5/14244 702/50
8,178,457 B2 5/2012 de Rochemont
8,193,873 B2 6/2012 Kato et al.
8,221,345 B2 7/2012 Blomquist
8,251,907 B2 8/2012 Sterling et al.
8,267,921 B2 9/2012 Yodfat et al.
8,350,657 B2 1/2013 deRochemont
8,354,294 B2 1/2013 de Rochemont et al.
8,449,524 B2 5/2013 Braig et al.
8,452,359 B2 5/2013 Rebec et al.
8,454,576 B2 6/2013 Mastrototaro et al.
8,467,980 B2 * 6/2013 Campbell ......... A61M 5/14244 702/50
8,478,557 B2 7/2013 Hayter et al.
8,547,239 B2 10/2013 Peatfield et al.
8,593,819 B2 11/2013 de Rochemont
8,597,274 B2 12/2013 Sloan et al.
8,622,988 B2 1/2014 Hayter
8,690,820 B2 * 4/2014 Cinar .................. A61M 5/1723 600/319
8,715,839 B2 5/2014 de Rochemont
8,810,394 B2 8/2014 Kalpin
8,939,935 B2 1/2015 OConnor et al.
9,061,097 B2 6/2015 Holt et al.
9,171,343 B1 10/2015 Fischell et al.
9,180,244 B2 11/2015 Anderson et al.
9,192,716 B2 11/2015 Jugl et al.
9,233,204 B2 1/2016 Booth et al.
9,364,609 B2 * 6/2016 Keenan ................. A61M 5/172
9,402,950 B2 8/2016 Dilanni et al.
9,486,571 B2 11/2016 Rosinko
9,520,649 B2 12/2016 de Rochemont
9,579,456 B2 2/2017 Budiman et al.
9,656,017 B2 5/2017 Greene
9,743,224 B2 8/2017 San Vicente et al.
9,857,090 B2 1/2018 Golden et al.
9,907,515 B2 3/2018 Doyle, III et al.
9,980,140 B1 5/2018 Spencer et al.
9,984,773 B2 5/2018 Gondhalekar et al.
10,010,669 B2 * 7/2018 Kamen ............. A61M 5/14586
10,248,839 B2 4/2019 Levy et al.
10,335,464 B1 7/2019 Michelich et al.
10,583,250 B2 3/2020 Mazlish et al.
10,646,650 B2 * 5/2020 Cinar ................. A61B 5/14532
10,737,024 B2 8/2020 Schmid
10,987,468 B2 4/2021 Mazlish et al.
11,197,964 B2 12/2021 Sjolund et al.
11,260,169 B2 3/2022 Estes
11,363,986 B2 * 6/2022 Vleugels ................ G16H 40/67
2001/0021803 A1 9/2001 Blank et al.
2001/0034023 A1 10/2001 Stanton, Jr. et al.
2001/0034502 A1 10/2001 Moberg et al.
2001/0048969 A1 12/2001 Constantino et al.
2001/0051377 A1 12/2001 Hammer et al.
2001/0053895 A1 12/2001 Vaillancourt
2001/0056258 A1 12/2001 Evans
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0047768 A1 4/2002 Duffy
2002/0070983 A1 6/2002 Kozub et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2002/0173769 A1 11/2002 Gray et al.
2002/0190818 A1 12/2002 Endou et al.
2003/0023148 A1 1/2003 Lorenz et al.
2003/0034124 A1 2/2003 Sugaya et al.
2003/0040715 A1 2/2003 DAntonio et al.
2003/0050621 A1 3/2003 Lebel et al.
2003/0060692 A1 3/2003 Ruchti et al.
2003/0086074 A1 5/2003 Braig et al.
2003/0086075 A1 5/2003 Braig et al.
2003/0090649 A1 5/2003 Sterling et al.
2003/0100040 A1 5/2003 Bonnecaze et al.
2003/0122647 A1 7/2003 Ou
2003/0130616 A1 7/2003 Steil et al.
2003/0135388 A1 7/2003 Martucci et al.
2003/0144582 A1 7/2003 Cohen et al.
2003/0148024 A1 8/2003 Kodas et al.
2003/0163097 A1 8/2003 Fleury et al.
2003/0170436 A1 9/2003 Sumi et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2003/0221621 A1 12/2003 Pokharna et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064088 A1 4/2004 Gorman et al.
2004/0064259 A1 4/2004 Haaland et al.
2004/0068224 A1 4/2004 Alfred, Jr. et al.
2004/0069044 A1 4/2004 Lavi et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0134609 A1 6/2005 Yu
2005/0137573 A1 6/2005 McLaughlin
2005/0171503 A1 8/2005 Van Den Berghe et al.
2005/0182306 A1 8/2005 Sloan
2005/0182366 A1 8/2005 Vogt et al.
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.

(56) References Cited

U.S. PATENT DOCUMENTS

2005/0261660 A1 11/2005 Choi
2005/0262451 A1 11/2005 Remignanti et al.
2005/0272640 A1 12/2005 Doyle, III et al.
2005/0277912 A1 12/2005 John
2006/0009727 A1 1/2006 OMahony et al.
2006/0041229 A1 2/2006 Garibotto et al.
2006/0079765 A1 4/2006 Neer et al.
2006/0079809 A1 4/2006 Goldberger et al.
2006/0086994 A1 4/2006 Viefers et al.
2006/0100494 A1 5/2006 Kroll
2006/0134323 A1 6/2006 OBrien
2006/0134491 A1 6/2006 Hilchenko et al.
2006/0167350 A1 7/2006 Monfre et al.
2006/0173406 A1 8/2006 Hayes et al.
2006/0178633 A1 8/2006 Garibotto et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0100635 A1 5/2007 Mahajan et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0166453 A1 7/2007 Van Duren et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0259768 A1 11/2007 Kear et al.
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051738 A1 2/2008 Griffin
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0114304 A1 5/2008 Nalesso et al.
2008/0132880 A1 6/2008 Buchman
2008/0160492 A1 7/2008 Campbell et al.
2008/0161664 A1 7/2008 Mastrototaro et al.
2008/0172026 A1 7/2008 Blomquist
2008/0172028 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2009/0326472 A1 12/2009 Carter
2010/0017141 A1 1/2010 Campbell et al.
2010/0036326 A1 2/2010 Matusch
2010/0057042 A1 3/2010 Hayter
2010/0064243 A1 3/2010 Buck et al.
2010/0077198 A1 3/2010 Buck et al.
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0185183 A1 7/2010 Alme et al.
2010/0211003 A1 8/2010 Sundar et al.
2010/0228110 A1 9/2010 Tsoukalis
2010/0241066 A1 9/2010 Hansen et al.
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0049394 A1 3/2011 de Rochemont
2011/0054390 A1 3/2011 Searle et al.
2011/0054399 A1 3/2011 Chong et al.
2011/0065224 A1 3/2011 Bollman et al.
2011/0071765 A1 3/2011 Yodfat et al.
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.
2011/0202005 A1 8/2011 Yodfat et al.
2011/0218495 A1 9/2011 Remde
2011/0230833 A1 9/2011 Landman et al.
2011/0251509 A1 10/2011 Beyhan et al.
2011/0313680 A1 12/2011 Doyle et al.
2011/0316562 A1 12/2011 Cefai et al.
2012/0003935 A1 1/2012 Lydon et al.
2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0124521 A1 5/2012 Guo
2012/0136336 A1 5/2012 Mastrototaro et al.
2012/0150446 A1 6/2012 Chang et al.
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.

(56) References Cited

U.S. PATENT DOCUMENTS

2012/0238851 A1 9/2012 Kamen et al.
2012/0250449 A1 10/2012 Nakano
2012/0271655 A1 10/2012 Knobel et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0158503 A1 6/2013 Kanderian, Jr. et al.
2013/0172695 A1 7/2013 Nielsen et al.
2013/0172710 A1 7/2013 Mears et al.
2013/0178791 A1 7/2013 Javitt
2013/0231642 A1 9/2013 Doyle et al.
2013/0245545 A1 9/2013 Arnold et al.
2013/0253472 A1 9/2013 Cabiri
2013/0261406 A1 10/2013 Rebec et al.
2013/0296792 A1 11/2013 Cabiri
2013/0296823 A1 11/2013 Melker et al.
2013/0298080 A1 11/2013 Griffin et al.
2013/0317753 A1 11/2013 Kamen et al.
2013/0332874 A1 12/2013 Rosinko et al.
2013/0338576 A1 12/2013 OConnor et al.
2013/0346858 A1 12/2013 Neyrinck
2014/0005633 A1 1/2014 Finan
2014/0018730 A1 1/2014 Muller-Pathle
2014/0032549 A1 1/2014 McDaniel et al.
2014/0066886 A1 3/2014 Roy et al.
2014/0074033 A1 3/2014 Sonderegger et al.
2014/0088428 A1 3/2014 Yang et al.
2014/0108046 A1 4/2014 Cabrera et al.
2014/0121635 A1 5/2014 Hayter
2014/0128839 A1 5/2014 Dilanni et al.
2014/0129951 A1 5/2014 Amin et al.
2014/0135880 A1 5/2014 Baumgartner et al.
2014/0142508 A1 5/2014 Dilanni et al.
2014/0146202 A1 5/2014 Boss et al.
2014/0171901 A1 6/2014 Langsdorf et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0025503 A1 1/2015 Searle et al.
2015/0041498 A1 2/2015 Kakiuchi et al.
2015/0120317 A1 4/2015 Mayou et al.
2015/0134265 A1 5/2015 Kohlbrecher et al.
2015/0134353 A1 5/2015 Ferrell et al.
2015/0165119 A1 6/2015 Palerm et al.
2015/0173674 A1 6/2015 Hayes et al.
2015/0193585 A1 7/2015 Sunna
2015/0202386 A1 7/2015 Brady et al.
2015/0205509 A1 7/2015 Scriven et al.
2015/0205511 A1 7/2015 Vinna et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0301691 A1 10/2015 Qin
2015/0306314 A1 10/2015 Doyle et al.
2015/0331995 A1 11/2015 Zhao et al.
2015/0351671 A1 12/2015 Vanslyke et al.
2015/0356250 A1 12/2015 Polimeni
2015/0366945 A1 12/2015 Greene et al.
2016/0015891 A1 1/2016 Papiorek
2016/0019352 A1 1/2016 Cohen et al.
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0220181 A1 8/2016 Rigooard et al.
2016/0228641 A1 8/2016 Gescheit et al.
2016/0243318 A1 8/2016 Despa et al.
2016/0256087 A1 9/2016 Doyle et al.
2016/0259889 A1 9/2016 Murtha et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0021096 A1 1/2017 Cole et al.
2017/0049386 A1 2/2017 Abraham et al.
2017/0131887 A1 5/2017 Kim et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 O'Connor et al.
2017/0189625 A1 7/2017 Cirillo et al.
2017/0216524 A1 8/2017 Haider et al.
2017/0239415 A1 8/2017 Hwang et al.
2017/0281877 A1 10/2017 Marlin et al.
2017/0296746 A1 10/2017 Chen et al.
2017/0311903 A1 11/2017 Davis et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0296757 A1 10/2018 Finan et al.
2018/0307515 A1 10/2018 Meller et al.
2018/0342317 A1 11/2018 Skirble et al.
2018/0369479 A1 12/2018 Hayter et al.
2019/0076600 A1 3/2019 Grosman et al.
2019/0095052 A1 3/2019 De Wever et al.
2019/0132801 A1 5/2019 Kamath et al.
2019/0184091 A1 6/2019 Sjolund et al.
2019/0240403 A1 8/2019 Palerm et al.
2019/0290844 A1 9/2019 Monirabbasi et al.
2019/0321545 A1 10/2019 Saint
2019/0336683 A1 11/2019 O'Connor et al.
2019/0336684 A1 11/2019 O'Connor et al.
2019/0348157 A1 11/2019 Booth et al.
2019/0374714 A1 12/2019 Rioux et al.
2020/0001006 A1 1/2020 Pizzochero et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0113515 A1 4/2020 O'Connor et al.
2020/0219625 A1 7/2020 Kahlbaugh
2020/0342974 A1 10/2020 Chen et al.
2021/0050085 A1 2/2021 Hayter et al.
2021/0077719 A1 3/2021 Cardinali et al.
2021/0098105 A1 4/2021 Lee et al.
2022/0023536 A1 1/2022 Graham et al.

FOREIGN PATENT DOCUMENTS

CN 1297140 A 5/2001
CN 101208699 A 6/2008
DE 4200595 A1 7/1993
DE 19756872 A1 7/1999
EP 0026056 A1 4/1981
EP 0341049 A2 11/1989
EP 0496305 A2 7/1992
EP 0549341 A1 6/1993

(56) References Cited

FOREIGN PATENT DOCUMENTS

| | | | | |
|---|---|---|---|---|
| EP | 0867196 | A2 | 9/1998 | |
| EP | 0939451 | A1 | 9/1999 | |
| EP | 1177802 | A1 | 2/2002 | |
| EP | 1376759 | A2 | 1/2004 | |
| EP | 1491144 | A1 | 12/2004 | |
| EP | 0801578 | B1 | 7/2006 | |
| EP | 2139382 | A1 | 1/2010 | |
| EP | 2397181 | A1 | 12/2011 | |
| EP | 2468338 | A1 | 6/2012 | |
| EP | 2666520 | A1 | 11/2013 | |
| EP | 2695573 | A2 | 2/2014 | |
| EP | 2703024 | A1 | 3/2014 | |
| EP | 2830499 | A1 | 2/2015 | |
| EP | 2943149 | A1 | 11/2015 | |
| EP | 3177344 | A1 | 6/2017 | |
| EP | 3193979 | A1 | 7/2017 | |
| EP | 3314548 | A1 | 5/2018 | |
| EP | 1571582 | B1 | 4/2019 | |
| EP | 2897071 | B1 | 5/2019 | |
| EP | 3607985 | A1 | 2/2020 | |
| EP | 3749183 | B1 * | 4/2024 | ......... A61B 5/14532 |
| FR | 2096275 | A5 | 2/1972 | |
| GB | 1125897 | A | 9/1968 | |
| GB | 2443261 | A | 4/2008 | |
| JP | 51125993 | A | 11/1976 | |
| JP | 02131777 | A | 5/1990 | |
| JP | 2005326943 | A | 11/2005 | |
| JP | 2004283378 | A | 10/2007 | |
| JP | 2008513142 | A | 5/2008 | |
| JP | 2010524639 | A | 7/2010 | |
| JP | 2012502693 | A | 2/2012 | |
| JP | 2017525451 | A | 9/2017 | |
| JP | 2018153569 | A | 10/2018 | |
| JP | 2019525276 | A | 9/2019 | |
| TW | 200740148 | A | 10/2007 | |
| TW | M452390 | U | 5/2013 | |
| WO | 200048112 | A2 | 9/1968 | |
| WO | 8606796 | A1 | 11/1986 | |
| WO | 9800193 | A1 | 1/1998 | |
| WO | 9855073 | A1 | 12/1998 | |
| WO | 9910040 | A1 | 3/1999 | |
| WO | 9910049 | A1 | 3/1999 | |
| WO | 9956803 | A1 | 11/1999 | |
| WO | 9962576 | A1 | 12/1999 | |
| WO | 0030705 | A1 | 6/2000 | |
| WO | 200032258 | A1 | 6/2000 | |
| WO | 0172354 | A2 | 10/2001 | |
| WO | 2001078812 | A1 | 10/2001 | |
| WO | 2002015954 | A1 | 2/2002 | |
| WO | 0226282 | A2 | 4/2002 | |
| WO | 2002043866 | A2 | 6/2002 | |
| WO | 2002076535 | A1 | 10/2002 | |
| WO | 2002082990 | A1 | 10/2002 | |
| WO | 2003016882 | A1 | 2/2003 | |
| WO | 2003039362 | A1 | 5/2003 | |
| WO | 2003045233 | A1 | 6/2003 | |
| WO | 2003097133 | A1 | 11/2003 | |
| WO | 2004043250 | A1 | 5/2004 | |
| WO | 2005110601 | A1 | 5/2004 | |
| WO | 2004092715 | A1 | 10/2004 | |
| WO | 2005051170 | A2 | 6/2005 | |
| WO | 2005082436 | A1 | 9/2005 | |
| WO | 2005113036 | A1 | 12/2005 | |
| WO | 2006053007 | A2 | 5/2006 | |
| WO | 2007064835 | A2 | 6/2007 | |
| WO | 2007066152 | A2 | 6/2007 | |
| WO | 2007078937 | A1 | 7/2007 | |
| WO | 2008024810 | A2 | 2/2008 | |
| WO | 2008029403 | A1 | 3/2008 | |
| WO | 2008133702 | A1 | 11/2008 | |
| WO | 2009039203 | A2 | 3/2009 | |
| WO | 2009045462 | A1 | 4/2009 | |
| WO | 2009049252 | A1 | 4/2009 | |
| WO | 2009066287 | A3 | 5/2009 | |
| WO | 2009066288 | A1 | 5/2009 | |
| WO | 2009098648 | A2 | 8/2009 | |
| WO | 2009134380 | A2 | 11/2009 | |
| WO | 2010022069 | A2 | 2/2010 | |
| WO | 2010053702 | A1 | 5/2010 | |
| WO | 2010077279 | A1 | 7/2010 | |
| WO | 2010132077 | A1 | 11/2010 | |
| WO | 2010138848 | A1 | 12/2010 | |
| WO | 2010139793 | A1 | 12/2010 | |
| WO | 2010147659 | A2 | 12/2010 | |
| WO | 2011031458 | A1 | 3/2011 | |
| WO | 2011075042 | A1 | 6/2011 | |
| WO | 2011095483 | A1 | 8/2011 | |
| WO | 2011133823 | A1 | 10/2011 | |
| WO | 2012045667 | A2 | 4/2012 | |
| WO | 2012073032 | A1 | 6/2012 | |
| WO | 2012108959 | A1 | 8/2012 | |
| WO | 2012134588 | A1 | 10/2012 | |
| WO | 2012177353 | A1 | 12/2012 | |
| WO | 2012178134 | A2 | 12/2012 | |
| WO | 2013050535 | A2 | 4/2013 | |
| WO | 2013078200 | A1 | 5/2013 | |
| WO | 2013134486 | A2 | 9/2013 | |
| WO | 20130149186 | A1 | 10/2013 | |
| WO | 2013177565 | A1 | 11/2013 | |
| WO | 2013182321 | A1 | 12/2013 | |
| WO | 2014029416 | A1 | 2/2014 | |
| WO | 2014109898 | A1 | 7/2014 | |
| WO | 2014110538 | A1 | 7/2014 | |
| WO | 2014149357 | A1 | 9/2014 | |
| WO | 2014179774 | A1 | 11/2014 | |
| WO | 2014194183 | A2 | 12/2014 | |
| WO | 2015056259 | A1 | 4/2015 | |
| WO | 2015061493 | A1 | 4/2015 | |
| WO | 2015073211 | A1 | 5/2015 | |
| WO | 2015081337 | A2 | 6/2015 | |
| WO | 2015117082 | A1 | 8/2015 | |
| WO | 2015117854 | A1 | 8/2015 | |
| WO | 2015167201 | A1 | 11/2015 | |
| WO | 2015177082 | A1 | 11/2015 | |
| WO | 2015187366 | A1 | 12/2015 | |
| WO | 2016004088 | A1 | 1/2016 | |
| WO | 2016022650 | A1 | 2/2016 | |
| WO | 2016041873 | A1 | 3/2016 | |
| WO | 2016089702 | A1 | 6/2016 | |
| WO | 2016141082 | A1 | 9/2016 | |
| WO | 2016161254 | A1 | 10/2016 | |
| WO | 2017004278 | A1 | 1/2017 | |
| WO | 2017091624 | A1 | 6/2017 | |
| WO | 2017105600 | A1 | 6/2017 | |
| WO | 2017184988 | A1 | 10/2017 | |
| WO | 2017187177 | A1 | 11/2017 | |
| WO | 2017205816 | A1 | 11/2017 | |
| WO | 2018009614 | A1 | 1/2018 | |
| WO | 2018067748 | A1 | 4/2018 | |
| WO | 2018120104 | A1 | 7/2018 | |
| WO | 2018136799 | A1 | 7/2018 | |
| WO | 2018204568 | A1 | 11/2018 | |
| WO | 2019077482 | A1 | 4/2019 | |
| WO | 2019094440 | A1 | 5/2019 | |
| WO | 2019213493 | A1 | 11/2019 | |
| WO | 2019246381 | A1 | 12/2019 | |
| WO | 2020081393 | A1 | 4/2020 | |
| WO | 2021011738 | A1 | 1/2021 | |
| WO | 2021096756 | A1 | 5/2021 | |
| WO | 2021236864 | A1 | 11/2021 | |
| WO | 2021253045 | A2 | 12/2021 | |

OTHER PUBLICATIONS

Blockeel et al., Decision trees: from efficient prediction to responsible AI, University of Granada, Spain, published: Jul. 26, 2023. (Year: 2023).*

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using

(56) References Cited

OTHER PUBLICATIONS

Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (Optis.247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73,1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

(56) References Cited

OTHER PUBLICATIONS

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
Andrenko et al., "EM Analysis of PBG Substrate Microstrip Circuits for Integrated Transmitter Front End" MMET Proceedings, 295-297 (2000).
Bardi et al., "Plane Wave Scattering From Frequency-Selective Surfaces by the Finite-Element Method" IEEE Transactions on Magnetics 38(2):641-644 (2002).
Chappell et al., "Composite Metamaterial Systems for Two-Dimensional Periodic Structures" IEEE, 3840387 (2002).
Cheng et al., "Preparation and Characterization of (Ba, Sr) TiO3 thin films using interdigitial electrodes" Microelectronic Engineering, 66:872-879 (2003).
Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).
Diaz et al., "Magnetic Loading of Antificial Magnetic Conductors for Bandwidth Enhancement" IEEE, 431-434 (2003).
Hansen "Effect of a High-Impedance Screen on a Dipole Antenna" IEEE Antennas and Wireless Propagation Letter, 1:46-49 (2002).
Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).
Kern et al., "Active Negative Impedance Loaded EBG Structures for the Realization of Ultra-Wideband Artificial Magnetic Conductors" IEEE, 427-430 (2003).
Kern et al., "The Synthesis of Metamaterial Ferrities for RF Applications Using Electromagnetic Bandgap Structures" IEEE, 497-500 (2003).
Kern et al., "Ultra-thin Electromagnetic Bandgap Absorbers Synthesized via Genetic Algorithms" IEEE, 1119-1122 (2003).
Kuhn et al., "Characterization of novel mono- and bifacially active semi-transparent crystalline silicon solar cells" IEEE Transactions on Electron Devices, 46(10): 2013-2017 (1999).
Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).
Lee et al., "Investigation of Electromagnetic Bandgap (EBG) Structures for Antenna Pattern Control" IEEE, 1115-1118 (2003).
Mckinzie III et al., "Mitigation of Multipath Through the Use of an Artificial Magnetic Conductor for Precision CPS Surveying Antennas" IEEE, 640-643.
Monorciho et al., "Synthesis of Artificial Magnetic Conductors by Using Multilatered Frequency Selective Surfaces" IEEE Antennas and Wireless Propagation Letters, 1:196-1999 (2002).
Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).
Pontes et al., "Study of the dielectric and ferroelectric properties of chemically processed BaxSr1—xTiO3 thin films" Thin Solid Films, 386(2)91-98 (2001).
Rogers et al., "AMCs Comprised of Interdigital Capacitor FSS Layers Enable Lower Cost Applications" IEEE, 411-414 (2003).
Sievenpiper et al., "Two-Dimensional Beam Steering Using an Electrically Tunable Impedance Surface" IEEE Transactions on Antennas and Propagation, 51(10):2713-2722(2003).
Sun et al., "Efficiency of Various Photonic Bandgap (PBG) Structures" 3rd Int'l. Conf. on Microwave and Millimeter Wave Technology Proceedings, 1055-1058 (2002).
Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).
Vest "Metallo-organic decomposition (MOD) processing of ferroelectric and electro-optic films: A review" Ferroelectrics, 102(1):53-68 (1990).
Viviani et al., "Positive Temperature Coefficient of Electrical Resistivity below 150k of Barium Strontium Titanate" J. Amer. Ceram. Soc. 87(4): 756-758 (2004).
Weily et al., "Antennas Based on 2-D and 3-D Electromagnetic Bandgap Materials" IEEE, 847-850 (2003).
Yang et al., "Surface Waves of Printed Antennas on Planar Artificial Periodic Dielectric Structures" IEEE Transactions on Antennas and Propagation 49(3): 444-450 (2001).
Zhang et al., "Planar Artificial magnetic Conductors and Patch Antennas" IEEE Transactions on Antennas and Propagation, 51(10):2704-2712 (2003).
Ziroff et al., "A Novel Approach for LTCC Packaging Using a PBG Structure for Shielding and Package Mode Suppression" 33rd European Microwave Conference—Munich 419-422 (2003).
International Search Report and Written Opinion for Application No. PCT/US17/61336, mailed on Jan. 25, 2018, 9 pages.
"Graph Chart." iconfinder.com. Aug. 15, 2016. Accessed Apr. 21, 2020. Available online at URL: https://www. confinder.com/iconsets/graph-chart-2>.
"Circular Progress Indicator Component for React." reactscript.com. Dec. 2, 2016. Accessed Sep. 9, 2020. Available online at URL: <http://reactscripts.com/circular-progress-indicator-component-react/>.
Kruska, Michal. "Circle progress bar." dribbble.com. Oct. 18, 2012. Accessed Apr. 21, 2020. Available online at URL: <https://dribbble.com/shots/775718-Circle-progress-bar>.
"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-xamarin-forms>.
International Search Report and Written Opinion for Application No. PCT/US2021/047685 mailed on Dec. 6, 2021, 15 pages.
Team Section—Qonto, by Christophe Kerebel, dated Dec. 12, 2018, dribbble.com [online]. Retrieved Jul. 1, 2022 from Internet <URL: https://dribbble.com/shots/5676730-Team-Section-Qonto> (Year: 2018).
"Circular Loader." dribbble.com. Nov. 19, 2015. Accessed Jul. 24, 2019. Available online at URL: https://dribbble.com/ shots/2362441-Circular-Loader (Year: 2015).
"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- -knobs-range-slider> (Year: 2015).
"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).
"Tick and cross circle shape icon . . . " depositphotos.com. Aug. 27, 2016. Accessed Feb. 1, 2019. Available online at URL:<https://depositphotos.com/121291612/stock-illustration-tick-and-cross-circle-shape.html> (Year: 2016).
"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- -of-preloader-buffer-shapes-or-dials-with-knobs.html> (Year. N/A).
Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).
Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.

(56) References Cited

OTHER PUBLICATIONS

International Search Report and Written Opinion for the International Patent Application No. PCT/US21/064056, mailed Apr. 4, 2022, 12 pages.
International Search Report and Written Opinion for the International Patent Application No. PCT/US21/064170, mailed Apr. 20, 2022, 12 pages.
Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al.: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2023/060726, mailed May 4, 2023, 10 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

(56) References Cited

OTHER PUBLICATIONS

Kaveh et al., “Blood Glucose Regulation via Double Loop Higher Order Sliding Mode Control and Multiple Sampling Rate.” Paper presented at the proceedings of the 17th IFAC World Congress, Seoul, Korea (Jul. 2008).
Dassau et al., “Real-Time Hypoglycemia Prediction Suite Using Contineous Glucose Monitoring,” Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., “Control-Relevant Models for Glucose Control using a Priori Patient Characteristics”, IEEE Transactions on Biomedical Engineering, vol. 59, No. 7, (Jul. 1, 2012) pp. 1839-1849.
Doyle III et al., “Run-to-Run Control Strategy for Diabetes Management.” Paper presented at 23rd Annual International Conference of the IEEE Engineering in Medicine and Biology Society, Istanbul, Turkey. (Oct. 2001).
Bequette, B.W., and Desemone, J., “Intelligent Dosing Systems”: Need for Design and Analysis Based on Control Theory, Diabetes Technology and Therapeutics 9(6): 868-873 (2004).
Parker et al., “A Model-Based Agorithm for Blood Gucose Control in Type 1 Diabetic Patients.” IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
“How to Create a QR Code that Deep Links to Your Mobile App”, Pure Oxygen Labs, web<https://pureoxygenlabs.com/how-to-create-a-qr-codes-that-deep-link-to-your-mobile-app/> Year:2017.
“Read NFC Tags with an iPHone App on iOS 11”, GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.

* cited by examiner

SYSTEMS AND METHODS FOR ENSURING SUFFICIENT BOLUS DOSING FOR MEAL COMPENSATION

RELATED APPLICATIONS

This application claims the benefit of U.S. Provisional Patent Application No. 63/300,460, filed Jan. 18, 2022, the contents of which are incorporated herein by reference in their entirety.

BACKGROUND

Many conventional automatic drug delivery systems are well known, including, for example, wearable drug delivery devices of the type shown in FIG. 2. The drug delivery device 102 can be designed to deliver any type of liquid drug to a user. In specific embodiments, the drug delivery device 102 can be, for example, an OmniPod® drug delivery device manufactured by Insulet Corporation of Acton, Massachusetts. The drug delivery device 102 can be a drug delivery device such as those described in U.S. Pat. Nos. 7,303,549, 7,137,964, or U.S. Pat. No. 6,740,059, each of which is incorporated herein by reference in its entirety.

Wearable drug delivery devices 102 are typically configured with a processor and memory and may execute a medication delivery algorithm (MDA). Alternatively, the medication delivery application may be executed on or via a remote device, such as a remote personal diabetes manager (PDM) or a smartphone, for example, which may be configured to transmit drug delivery instructions to the wearable drug delivery device 102.

The MDA may provide for basal dosing of a liquid drug. For example, for diabetics, the MDA may provide for basal doses of insulin or co-formulations of insulin and other drugs, to be delivered to the user, while allowing the user to self-administer bolus doses of the liquid drug to compensate for post-prandial excursions in the blood glucose level of the user.

The usual procedure for a user to self-administer a meal bolus is to use a bolus calculator to calculate the proper bolus dose to compensate for the ingested meal. To use the bolus calculator, the user enters the number of carbohydrates in the meal and the bolus dose is calculated based on the user's insulin to carbohydrate ratio. Typically, the bolus dose is the number of grams of carbohydrates in the meal divided by the insulin to carbohydrate ratio).

$$\text{Bolus Insulin} = \frac{\text{Number of Grams of Carbohydrates}}{\text{Insulin to Carbohydrate Ratio}}$$

However, this method is error prone, as the user often mis-estimates the number of carbohydrates in the meal. Additionally, the insulin to carbohydrate ratio may vary throughout the day, depending on recent exercise activity, stress levels and hormonal variations. A dangerous situation could arise if the user administers an excessive or insufficient amount of insulin.

In addition, experienced users may become comfortable with the use of automatic insulin delivery (AID) systems and may become complacent in the self-administration of bolus doses of the liquid drug by inadvertently decreasing the number of times they bolus for their meals. The user may therefore have increased instances where their meals may not be sufficiently manually compensated with boluses. In addition, there may be occasions when a meal bolus is delayed, or a bolus is taken in anticipation of a meal, but the meal is delayed.

Given the many variables surrounding the self-administration of bolus doses, it is desirable to provide some level of safety for the user by building in several safeguards to the MDA which may be capable of compensating for, or at least alerting the user of, anomalous situations which may arise due to the shortcomings inherent in the self-administration of bolus doses.

Definitions

As used herein, the term "liquid drug" should be interpreted to include any drug in liquid form capable of being administered by a drug delivery device via a subcutaneous cannula, including, for example, insulin, GLP-1, pramlintide, morphine, blood pressure medicines, chemotherapy drugs, fertility drugs or the like or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In a first embodiment, the MDA may be configured to provide safeguards against or compensate for insufficient deliveries of bolus doses of the liquid drug. In a first aspect, various innovative features may be built into the MDA to provide for a safe calculation of a bolus dose to be automatically administered by the drug delivery device. The innovative features will be discussed in greater detail below. In a second aspect of the invention, the MDA may be able to assess past glucose history to automatically determine whether the user has ingested a meal that was not manually compensated for or was under-compensated for. When it has been determined that the user has ingested a meal, in a third aspect of the invention, the MDA may provide metrics to the user and may increase the aggressiveness of the MDA for high glucose concentrations during these periods. In a fourth aspect of the invention, when the MDA determines that a meal has been ingested, a bolus dose of insulin may be automatically delivered by drug delivery device 102.

In various embodiments, the medication delivery algorithm may provide all or any combination of the above noted aspects of the invention.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

This disclosure presents various systems, components and methods for providing safeguards against inadequate bolus dosing when the user is self-administering the bolus doses. The embodiments described herein provide one or more advantages over conventional, prior art systems, components and methods, namely, the provision of a safety net for the user in the event that the user's self-administering of bolus doses is inadequate through safeguards built into the medication delivery algorithm.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, smart jewelry, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
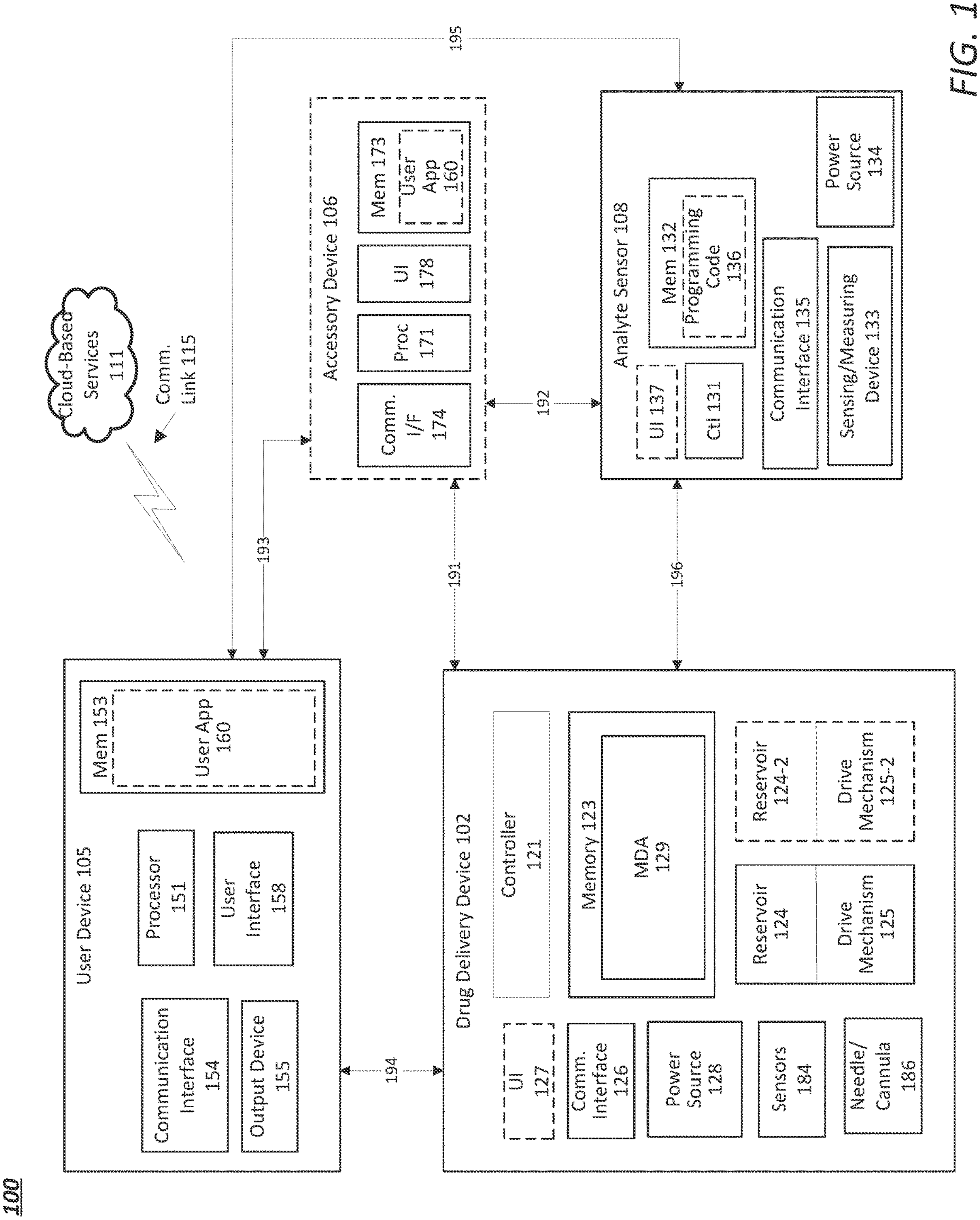
FIG. 1 illustrates a functional block diagram of an exemplary system suitable for implementing the systems and methods disclosed herein.
Figure 2:
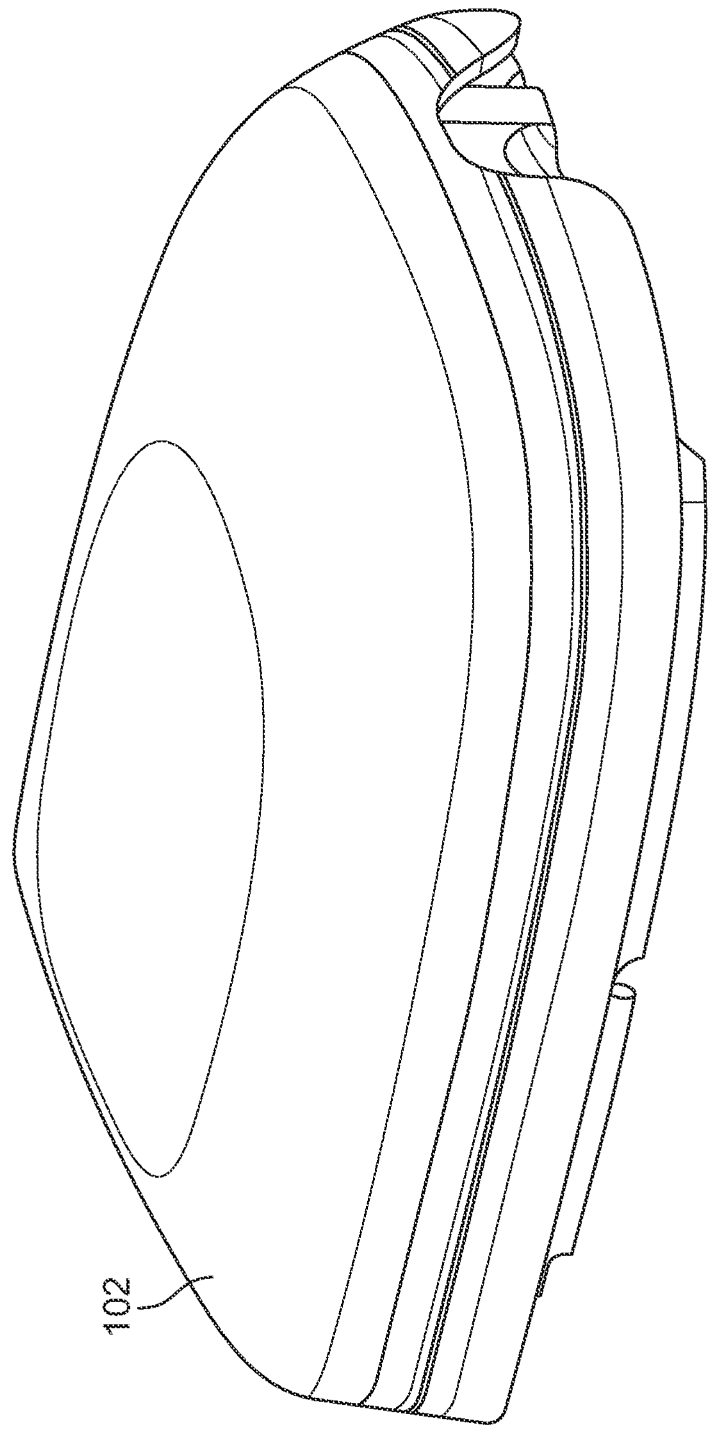
FIG. 2 is a depiction of a prior art wearable drug delivery device of the type in which the invention disclosed herein would be used.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like, as discussed below. The user device 105 may be used to program, adjust settings, and/or control operation of drug delivery device 102 and/or the analyte sensor 108 as well as the optional smart accessory device 106.

The processor 151 may also be configured to execute programming code stored in device memory 153, such as the user app 160. The user app 160 may be a computer application that is operable to deliver a drug based on information received from the analyte sensor 108, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may provide further functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123 onboard the drug delivery device (and in exemplary embodiments, a wearable drug delivery device). Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface 186 may be, for example, a needle or cannula for delivering the drug into the body of the user (which may be done subcutaneously, intraperitoneally, or intravenously). Drug delivery device 102 may further include a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, IOB, insulin remaining, and the like, and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be a continuous glucose monitor (CGM) configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or in a housing attachable to the housing of drug delivery device 102 or otherwise adjacent thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set basal profiles for different times of day or temporary basal profiles. The controller 121 will also have the ability to function as a sensor-augmented pump in manual mode, using sensor glucose data provided by the analyte sensor 108 to populate the bolus calculator.

User app 160 may be configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm, and IOB may be divided between a basal IOB and a bolus IOB, the basal IOB accounting for insulin delivered by the algorithm, and the bolus IOB accounting for any bolus deliveries.

Description of Embodiments

The primary embodiment of the invention is directed to improvements implemented in an automatic drug delivery system 100, an example of which is shown in FIG. 1. The improvements are designed to make it easier for a user to maintain safe blood glucose levels. In one embodiment, the improvements eliminate the necessity for the user calculate and administer a bolus dose by providing a safe bolus dose to the user upon a notification of a meal event and thereafter providing further required dosing of the liquid drug in accordance with MDA 129. In other embodiments, drug delivery system 100 will automatically maintain acceptable glucose levels even when the user fails to self-administer a bolus dose of insulin prior to or after ingesting a meal.

The improvements may be implemented, for example, by modifications to the software executing as part of drug delivery system 100 (i.e., user application 160 or MDA 129). In certain embodiments, certain features may be implemented in user app 160 executing on user device 105, while other features may be implemented in MDA 129 executing on drug delivery device 102. Because various functions may be shared between user application 160 and MDA 129, the user application 160 and MDA 129 will be referred to herein collectively as the “system software”.

Figure 3:
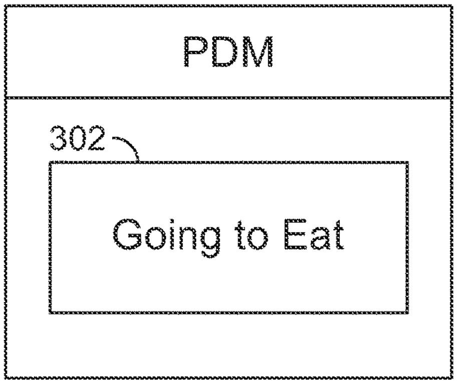
FIG. 3 is an exemplary user interface screen showing a "Going to Eat" button used to inform the system software that the user is about to ingest a meal.

In one embodiment, the user is provided with a “Going to Eat” user selectable button 302, shown in FIG. 3, which, when selected by the user, indicates a meal event to the system software. (i.e., that the user intends to eat a meal). In certain embodiments, MDA 129, upon receipt of a notification of a meal event, may replace the bolus calculator and eliminate the need for the user to enter the carbohydrate profile of the intended meal. In preferred embodiments of the invention, button 302 may be displayed in user interface 158 of user device 105 or, in alternate embodiments, in user interface 178 on accessory device 106. In other embodiments, when drug delivery device 102 is provided with a user interface 127, the user may notify the system software of a meal event by providing input directly to drug delivery device 102 via user interface 127 (in this instance, however, no graphical representation of button 302 will be displayed). Upon a user selection of “Going to Eat” button 302 (or, upon provision of an indication to drug delivery device 102 of a meal event) a safe bolus insulin dose will be calculated and delivered to the user, the calculation of the safe bolus does takes into consideration the user’s current blood glucose level, the insulin-on-board (IOB), the user’s glucose trend during a predetermined past period of time (in preferred embodiments, 30 minutes) and, whether nighttime mode is enabled. Each of these considerations will be explained later herein.

Figure 4:
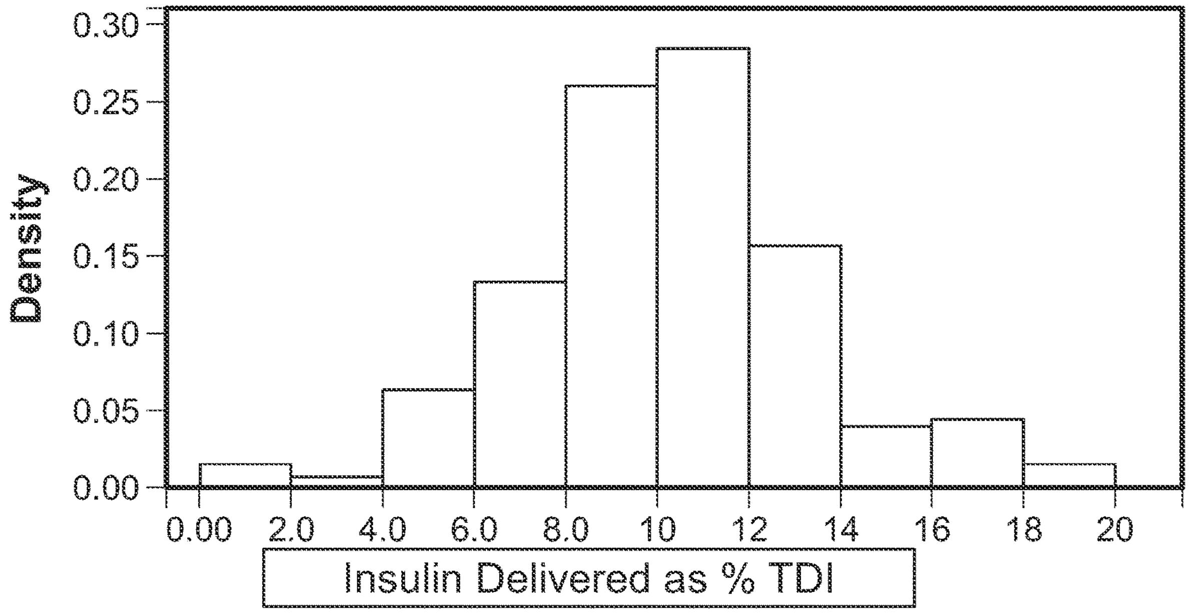
FIG. 4 is a histogram showing insulin delivered for each meal as a percentage of the user's TDI.

An analysis of the insulin delivered prior to meals is depicted in the histogram shown in FIG. 4. The histogram shows the insulin delivered as a percentage of the total daily insulin (TDI) versus density for a typical user. A safe nominal insulin dose, which may be adjusted by various considerations to determine a safe bolus dose, may be expressed as a percentage of the user’s total daily insulin (TDI) as:

$$\text{Safe Nominal Insulin Dose} = x * TDI \tag{1}$$

where:

x is the desired percentage; and

TDI is the user’s total daily insulin.

In one embodiment, x may be chosen as, for example, 8%, although other percentages may be chosen on a user-by-user basis. For example, a percentage between 5% to 15% (inclusive of endpoints) may be used for x.

In another aspect of the invention, a safe correction dose of insulin (IOB Required Safe) may be calculated based on the user’s current blood glucose level, an elevated threshold glucose value and a correction factor (based on, for example, the 1600 rule, which estimates the drop in blood glucose level per unit of insulin by dividing a 1600 factor by the TDI, as shown in Eq. 2 below). A safe correction dose may, in some embodiments, be expressed as:

$$IOB \text{ Required Safe} = \frac{BG_{current} - T_{Elevated}}{1600/TDI} \tag{2}$$

Where:

$BG_{current}$ is the user’s current blood glucose reading; and $T_{Elevated}$ is an elevated threshold.

In one embodiment, $T_{Elevated}$ may be set, for example, to 150 mg/dl, although any value for the $T_{Elevated}$ may be used. The elevated threshold is used in combination with the safe nominal insulin dose and the IOB to determine the safe bolus dose. The safe correction dose serves two purposes. First, it makes the insulin requirement safe and, second, it allows some flexibility for any delays in the ingestion of the meal after the user has indicated the intention to ingest a meal by selection of the “Going to Eat” button 302.

In the event that data from the CGM is missing, a minimum CGM value in the past 30 minutes may be used for the $BG_{current}$ value. In the event no valid CGM data is available for the last 30 minutes, the IOB Required Safe could be calculated as:

$$IOB \text{ Required Safe} = \frac{T_{Low} - T_{Elevated}}{1600/TDI} \tag{3}$$

where:

$T_{Low}$ is a low threshold.

The value of $T_{Low}$ may be set, in certain embodiments, to 100 ml/dl 70 ml/dl or 40 ml/dl, although any value for the low threshold may be used. Because the low threshold is always less than the elevated threshold, the use of the low threshold will lead to the IOB Required Safe to be negative and will reduce the total insulin.

In some embodiments, the safe bolus dose calculated and delivered after the user presses the "Going to Eat" button 302 can be further adjusted by a trend correction factor ($CF_T$) which depends on the trend of the blood glucose readings of the user for a predetermined time period prior to the selection of button 302. In certain embodiments, the predetermined time period may be, for example, 30 minutes. In preferred embodiments of the invention, blood glucose readings are periodically received from the CGM every five minutes, although, in other embodiments, other periods may be used. For embodiments wherein the receipt of the CGM readings occurs in five minute intervals, a prior 30 minute time period will result in 7 blood glucose readings, starting with the current blood glucose reading $BG_i$.

A trend may be detected by calculating a coarse slope and coarse curvature of the blood glucose readings over time. In one embodiment, the trend may be calculated by first calculating averages of ranges of blood glucose readings over 15-minute blocks as:

$$BG_{avg1} = \frac{BG_i + BG_{i-1} + BG_{i-2} + BG_{i-3}}{4} \quad (4)$$

$$BG_{avg2} = \frac{BG_{i-3} + BG_{i-4} + BG_{i-5} + BG_{i-6}}{4} \quad (5)$$

$$Range1 = BG_{i-3} - BG_i \quad (6)$$

$$Range2 = BG_{i-6} - BG_{i-4} \quad (7)$$

The coarse slope and coarse curvature may thereafter be defined as:

$$Slope_{coarse} = BG_{avg1} - BG_{avg2} \quad (8)$$

$$\text{Curvature}_{coarse} = \text{Range2} - \text{Range1} \quad (10)$$

In certain embodiments, a trend correction factor $CF_T$ may be determined using a set of rules. Although any set of rules may be used, in an exemplary embodiment, the set of rules may determine $CF_T$ as follows:

$$\text{If Slope}_{coarse} < 0 \text{ AND Curvature}_{coarse} < 0 \text{ then } CF_T = 0.5 \quad (11)$$

$$\text{If Range1} < 0 \text{ AND Range2} < 0 \text{ then } CF_T = 0.5 \quad (12)$$

$$\text{If Slope}_{coarse} < 0 \text{ then } CF_T = 0.5 \quad (13)$$

In the event that one or more CGM values during the predetermined past time period are missing or unavailable, a data quality metric may be used to determine if adequate CGM data is available make a trend decision. Such metrics may be, for example, no more than x % (e.g., 30%) of data points are missing in the last 30 minutes. If the data quality is unacceptable, no trend correction is made, and the $CF_T$ is set to 1.

If the user has experienced a hypoglycemic event just prior to the bolus dosing triggered by the notification of the meal event, (e.g., hypoglycemia within an hour or within a threshold time limit), then a rebound from hypo factor ($HF_{Rebound}$) that reduces the safe bolus dose can be applied. The hypo rebound factor may be specified as:

$$HF_{Rebound} = z$$

where:

z=0.75 in some embodiments or any other constant in other embodiments.

Figure 5:
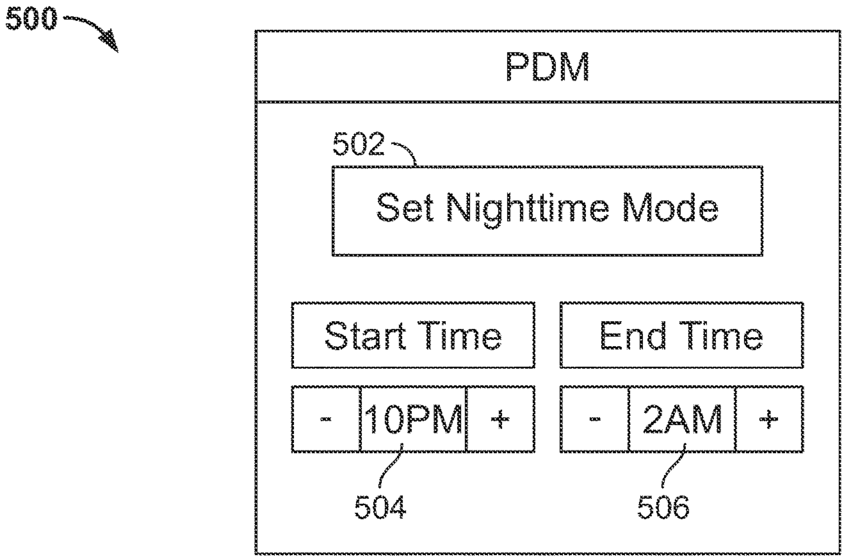
FIG. 5 is an exemplary user interface screen showing a "Set Nighttime Mode" button and fields for entering the start and end times of nighttime mode.

In some embodiments, a nighttime mode setting may be provided. The nighttime mode setting, if enabled, will further reduce the safe bolus dose to further reduce the risk of hypoglycemia. In one embodiment, the user is provided with a nighttime mode user interface screen 500, shown in FIG. 5, which includes a "Set Nighttime Mode" user selectable button 502 which, when selected by the user, indicates to the system software that nighttime mode is enabled. The user may set a start time 504 and an end time 506 to indicate when nighttime mode will be enforced.

In an alternative embodiment, nighttime mode can be enabled automatically by using an inertial measurement unit (IMU) sensor on the pump. The IMU may comprise one or more of an accelerometer, a gyro and, often, magnetometers. These sensors, together, can determine motion, orientation (or tilt) of the device in one or more of x, y, and z axes. For sustained activity such as running, swimming or sleeping, the IMU generates a unique profile of signal activity on each of the axes. By decoding these signals, a unique signature is identified which can be mapped to an activity. Thus, if it is determined that the user is sleeping, a unique signature would be detected along the 3 axes, and, together with time-zone information, a determination of "nighttime" mode for the user can be made.

In preferred embodiments of the invention, the nighttime mode user interface screen 500 may be displayed in user interface 158 of user device 105 or, in alternate embodiments, in user interface 178 on accessory device 106. In other embodiments, when drug delivery device 102 is provided with a user interface 127, the user may initiate nighttime mode directly to drug delivery device 102 via user interface 127 (in this instance, however, the nighttime mode user interface screen 500 will not be displayed).

If the nighttime mode is in effect and the "Going to Eat" button 302 is pressed, then a nighttime factor (NF) can be set which can vary from, for example, 0.6 to 0.9. In some embodiments, a value of 0.75 may be set as the default. The value can be reduced if, in past occurrences, the current value had created an additional risk of hypoglycemia. Conversely the current value can be increased if, in past occurrences, the blood glucose was elevated.

Figure 6:
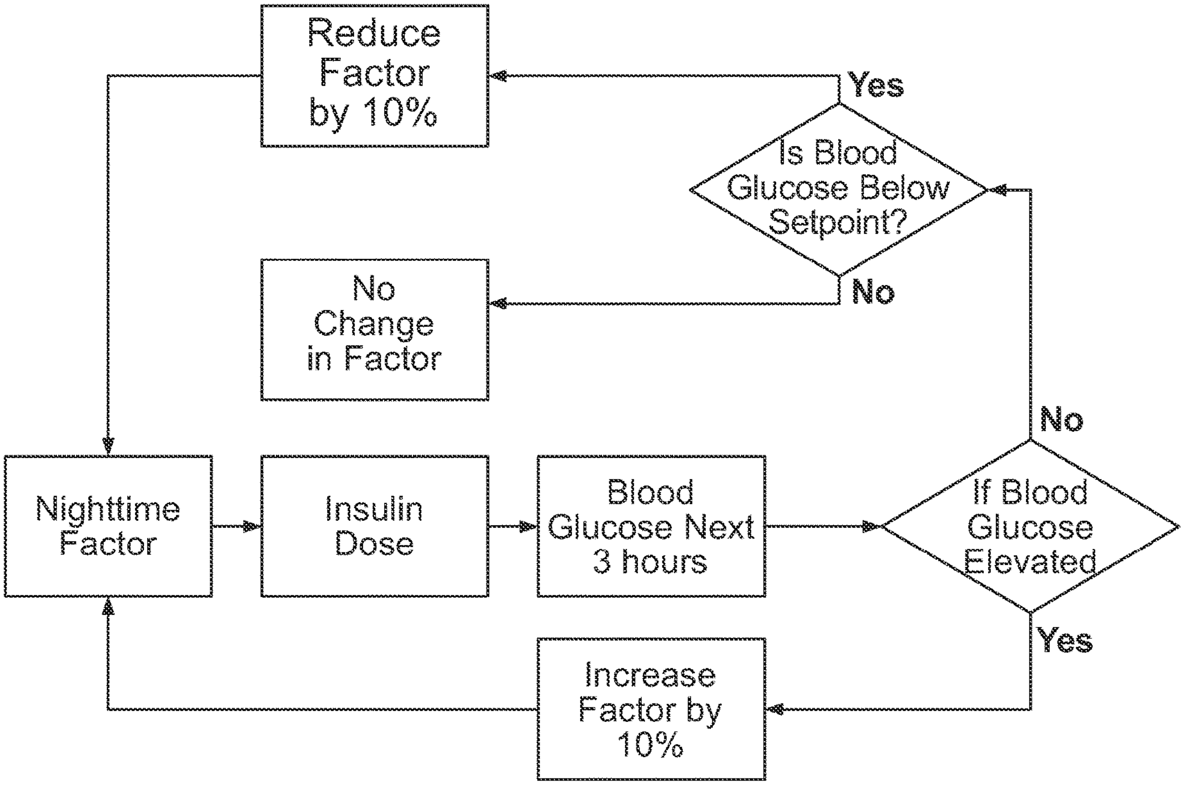
FIG. 6 is a flowchart showing how the nighttime factor is adjusted based on the previous delivery of insulin.

The flowchart shown in FIG. 6 may be used to determine any adjustments to the NF based on readings of the user's blood glucose levels over a three-hour time period in past occurrences when the safe bolus dose was delivered. Starting with the current NF, a safe bolus dose is delivered and the blood glucose is monitored for a predetermined time period, for example, for 3 hours. If the blood glucose became elevated, the current NF is increased by, for example, 10%, for the next calculation. Elevated blood glucose can be defined, in some embodiments, as blood glucose greater than 80 mg/dl over the setpoint at the 3-hour mark. Other values may be used, such as 50 mg/dl, 60 mg/dl, 70 mg/dl, 90 mg/dl, or 100 mg/dl over the setpoint at the 3-hour mark. In other embodiments, other criteria may be used. If the blood glucose is not elevated, it is determined if the blood glucose fell below a low setpoint. If not, no changes are made to the current NF. However, if the blood glucose fell below the setpoint, the NF may be reduced by, for example, 10% for the next calculation.

In certain embodiments, any combination of the trend factor, the rebound hypo factor and the nighttime factor may be applied to the safe bolus dose to modify the quantity of the liquid drug represented by the safe bolus dose and which is delivered to the user in response to the user selection of button 302. When using all factors previously explained, the safe bolus insulin dose can be expressed as:

$$(CF_T * HF_{Rebound} * NF * x * TDI) + IOB \text{ Required Safe} - IOB \tag{14}$$

where:

the $CF_T$, the $HF_{Rebound}$ and the NF modify the value of x for safety. In various embodiments, a safe bolus dose may take into account the trend factor, the rebound hypo factor, and the nighttime factor, or any combination (including none of these factors) thereof to calculate a safe bolus dose.

The IOB is the insulin-on-board from prior insulin deliveries. If the IOB is negative, then it is truncated to 0.

The safe bolus dose is best suited for closed loop systems where the algorithmic (basal) insulin can be safely increased to compensate for the safe bolus dose and greatly reduces the risk of hypoglycemia in closed loop systems. After the safe bolus dose is administered upon notification of the meal event, the system software of drug delivery device 100 will compensate for further post-prandial excursions in the user's blood glucose levels in accordance with algorithmic basal insulin delivery embodied by MDA 129.

Insulin may be delivered in accordance with Eq. (14) multiple times when the value of x is reduced. For example, x may be set or reduced to 3.5% due to the application of the various previously-explained factors and the initial bolus insulin delivery can administered when the user selects the "Going to Eat" button 302, with a second bolus administered 10 minutes thereafter and a third bolus 20 minutes thereafter. Trends in the blood glucose can be used to deliver insulin safely. The IOB safeguards against excess insulin delivery.

Detecting Un-bolused or Under-bolused Meals—In this aspect of the invention, a method is disclosed to assess past glucose history and to determine whether the user had a meal that was not manually compensated for or was undercompensated for via a self-administered bolus dose and for situations where the user fails to inform drug delivery system 100 of a meal and event by selection of button 302. In an extension of this embodiment, should an uncompensated or undercompensated meal be detected, the system software may provide metrics for the user, and may also increase the aggressiveness of MDA 129 for high glucose concentrations during those periods.

A typical un-bolused or under-bolused meals can result in significant increases in the user's glucose, and significant increases in the automated insulin delivery beyond basal. In one embodiment of this aspect of the invention, the system software can review 5-hour windows at a 5-minute moving increment across each 24-hour period, as follows:

$$W_{post,i=1 \ldots 228} = \sum_{j=1}^{60} I_{alg}(i+j) \tag{15}$$

$$G_{post,i=1 \ldots 228} = \frac{\sum_{j=1}^{60} G(i+j)}{60} \tag{16}$$

where:

$W_{post}$ is the total insulin delivered during the most recent 5-hour window;

$G_{post}$ is the average of the glucose readings for the most recent 5-hour window; and $I_{alg}$ is the insulin recommended by the medication delivery algorithm;

228 is the number of 5-hour windows in one day; and 60 is a number of 5-minute cycles in 5 hours.

As would be realized by one of skill in the art, the constants in the above equations are tunable parameters. Different periodic intervals for evaluating the equations or a different window size would dictate the use of appropriately different constants.

If $W_{post}$ and $G_{post}$ meet certain criteria, all data points for that specific period can be considered to meet the definition of an unannounced meal detection. In one embodiment, these criteria can be, for example:

$$P_i = \begin{cases} \text{True} & W_{post,i} > \frac{TDI}{48} \cdot 2 \cdot 5 \text{ AND } G_{post,i} > 180 \\ \text{False} & W_{post,i} \le \frac{TDI}{48} \cdot 2 \cdot 5 \text{ OR } G_{post,i} \le 180 \end{cases} \tag{17}$$

Here, the thresholds are at least 2 times the user's TDI-based basal being delivered over the most recent 5-hour window and the user's mean glucose is above 180 over the most recent 5-hour window. It is important to note that the specific numerical values introduced in this embodiment are all variable parameters. For instance, both the increments and total duration of moving windows can vary, such as reviewing 6-hour windows in every 30-minute increments, or 3-hour windows in every 15-minute increments, or other values. Moreover, the thresholds of selection criteria may also vary. For instance, the threshold of total increased automated insulin delivery can be of 1.5, 3 or 4 times basal compared to 2 times basal delivery. The final glucose concentration can also vary as different values, such as 150 mg/dL, 250 mg/dL, the user's final glucose target, other values.

The user's mean glucose concentration during each moving window can also be included as a condition, as an addition, or in replacement of, the ending glucose condition, with associated thresholds of detection. For example, the condition may be stated as a mean glucose higher than 150 mg/dL during the moving window.

Rather than a binary detection of meals during this period, the system may instead provide a probabilistic calculation of the occurrence of meals depending on the extent over which each condition is exceeded. For instance, the system may provide a 50% chance that an unannounced or under-bolused meal had occurred if the automated insulin delivery exceeded 1.5× basal over the 5-hour window, which may rise to 100% chance if the delivery exceeded 3× basal during this same period. Each condition may provide a probability of meal delivery, and the final determination of the probability of occurrence of a meal can be calculated as a mean, a sum, or other combination of the assessment of probability of a meal across all conditions.

For each period where an unannounced meal is detected, the user can be informed that the system detected that the user had an unannounced meal. In addition, the system software can provide a recommended amount of insulin based on the user's final glucose at the end of the period that, had the user self-administered a bolus of that amount, the user's glucose control outcomes would have been improved:

$$I_{rec,i} = \frac{G(i+60) - \text{target } (i+60)}{CF(i)} \tag{18}$$

Further, the system software may respond more aggressively to glucose deviations during the first 90 minutes of this period, by reducing the Q:R ratio (relative cost of insulin deviation-vs-glucose deviation) during this period based on the additional required insulin, as follows:

$$Q_{new,i \, \ldots \, i+18} = \max\left(Q_{base}\left(\frac{I_{rec,i}}{\frac{TDI}{48}\cdot 2\cdot 1.5}, Q_{base}\right)\right) \tag{19}$$

In another aspect of the invention, a machine learning approach may be used to perform the detection of a meal. In this embodiment, a meal can be detected based on machine learning models that detect the characteristic rising profile of the blood sugar levels. The meal detection models are preferably trained on a closed loop control dataset. Blood glucose profiles from closed loop data with prescribed rising characteristics are labeled to be used as training data. In one embodiment, the rise characteristics can be, for example, 20 ml/dl within a 15 minute period, 40 ml/dl within a 30 minute period and 60 ml/dl within a 60 minute period.

In one embodiment, two-hour periods of blood glucose data that go back in time from 10 minutes after the initial blood glucose rise, 15 minutes after the initial blood glucose rise and 20 minutes after the initial blood glucose rise, are trained using decision trees for detecting meals.

Figure 7:
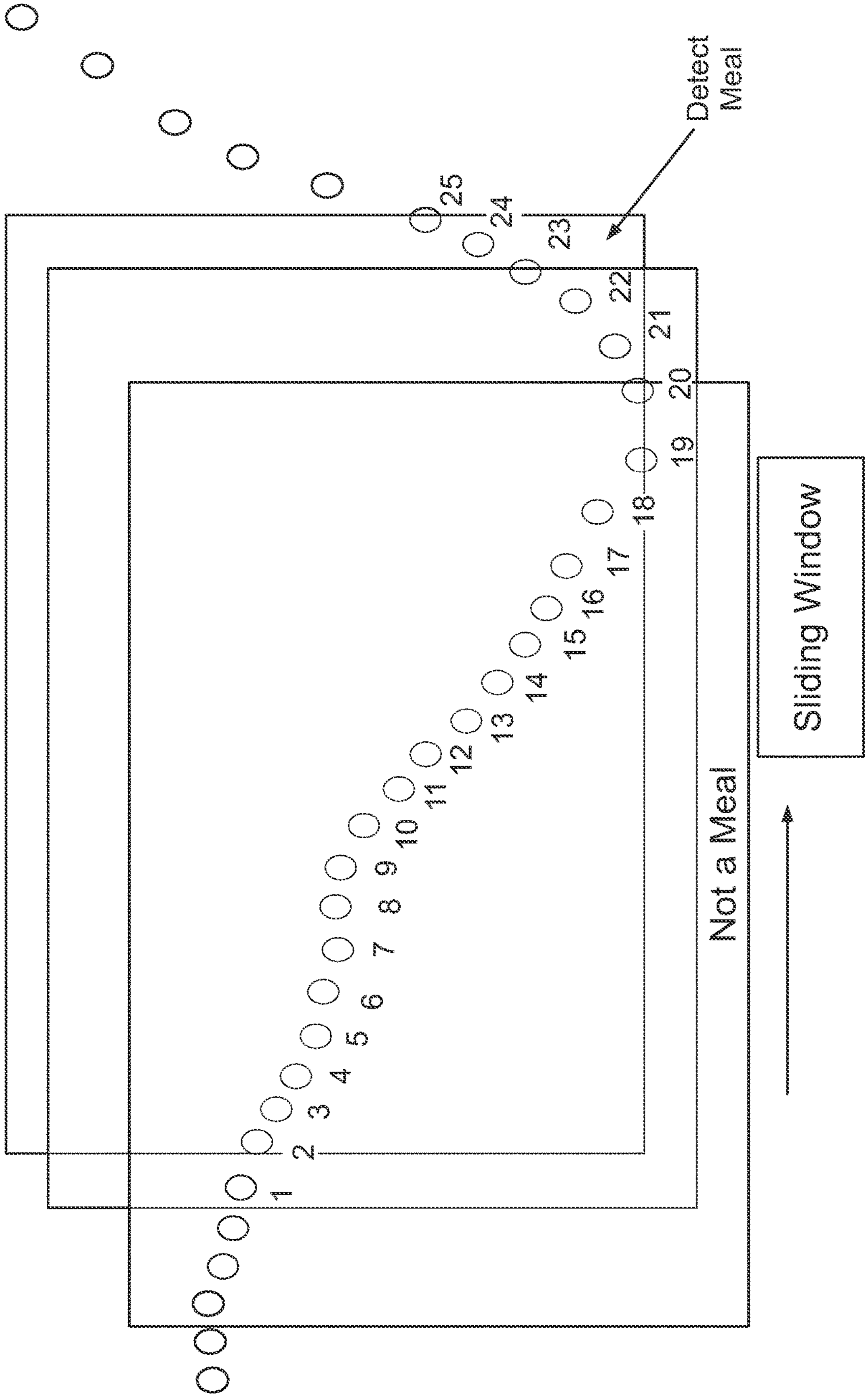
FIG. 7 is a plot of blood glucose readings having a sliding window superimposed thereon used to detect meals.
Figure 8:
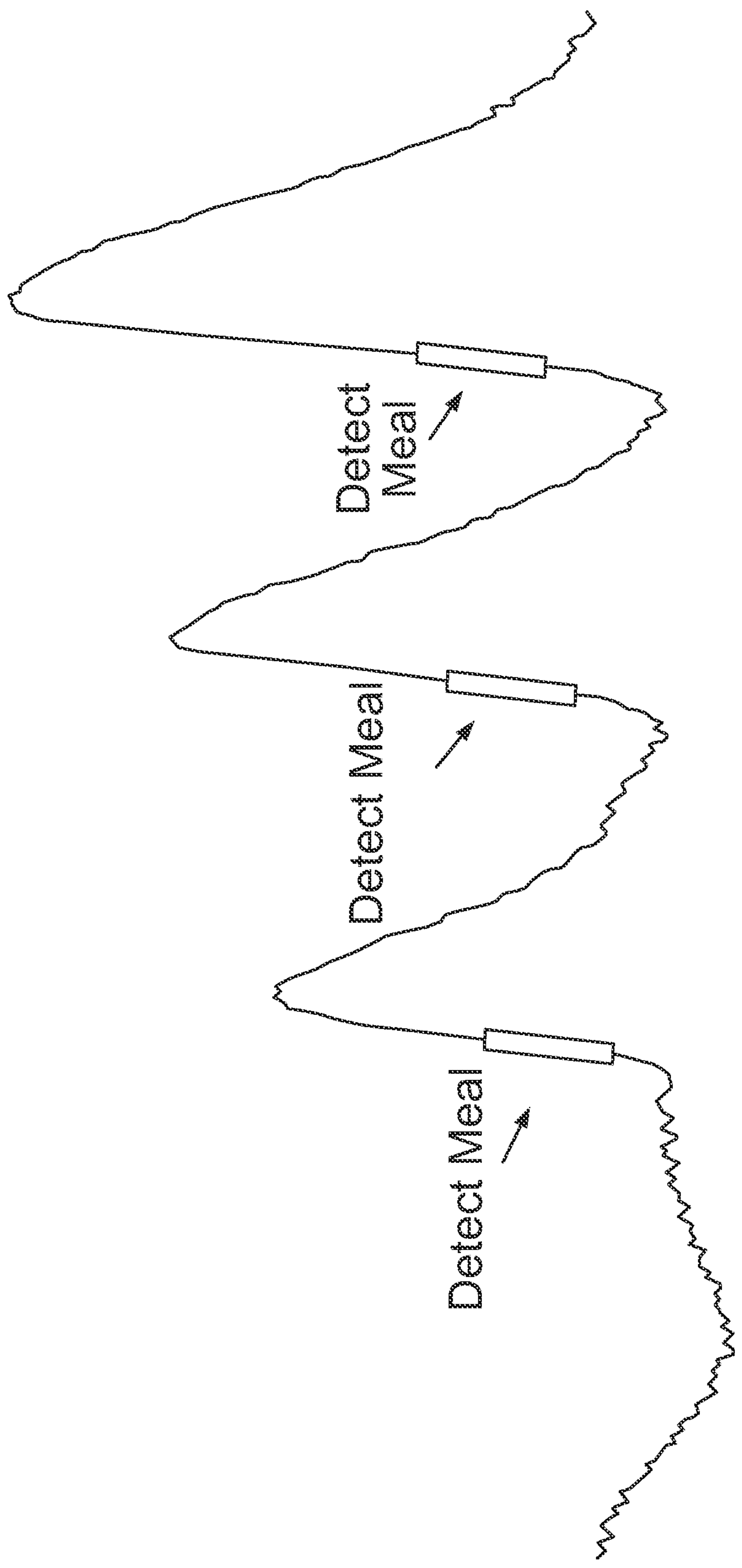
FIG. 8 is a plot of blood glucose readings over a period of the day showing rising glucose levels when meals have been ingested and the portions of the plot used to detect the meals.

FIG. 7 shows a sliding window over a plot of the blood glucose levels used to detect meals. As the window indexes through time, a meal is detected, in this example, when the sliding window reaches BG points 23, 24, 25 and beyond. FIG. 8 shows a relationship between blood glucose rise and meal detection. A three-meal day pattern is shown.

To detect meals, certain features will be detected in the blood glucose data. In one embodiment, a 2-hour history of blood glucose data is maintained. In this embodiment, blood glucose may be sampled every five minutes, resulting in 25 data points. In embodiments wherein a different history period or different intervals for the sampling of the blood glucose levels are used, a different number of data points will be available for analysis. In one embodiment of the invention, the following features may be detected: 15 minute averages (average blood glucose in every 15 minute period during the most recent two-hour history); range features (differences in the blood glucose levels every 15 minutes); delta values (differences of 15 minute averages, providing coarse slopes of the plot of the blood glucose levels); slope values (differences between consecutive values of the slope of the plot of the blood glucose levels); and second derivatives (the differences of the slopes of the plot of the blood glucose levels). In other embodiments of the invention, other features may be used.

In the training phase, blood glucose data is identified with rise characteristics such as 20 ml/dl within a 15 minute period, 40 ml/dl within a 30 minute period and 60 ml/dl within a 60 minute period. The identified data is presented to a machine learning model to develop meal detection rules. It should be noted that, while the full upward rising portion of the blood glucose curve is used to recognize a post-prandial rise in the glucose levels, in one embodiment, only 10-minutes, 15-minutes and 20-minutes of the rising blood glucose curve (and values earlier for a total of 25 data points at each instant), are presented to the machine learning system. The objective is to detect meals with minimal latency.

Figure 9:
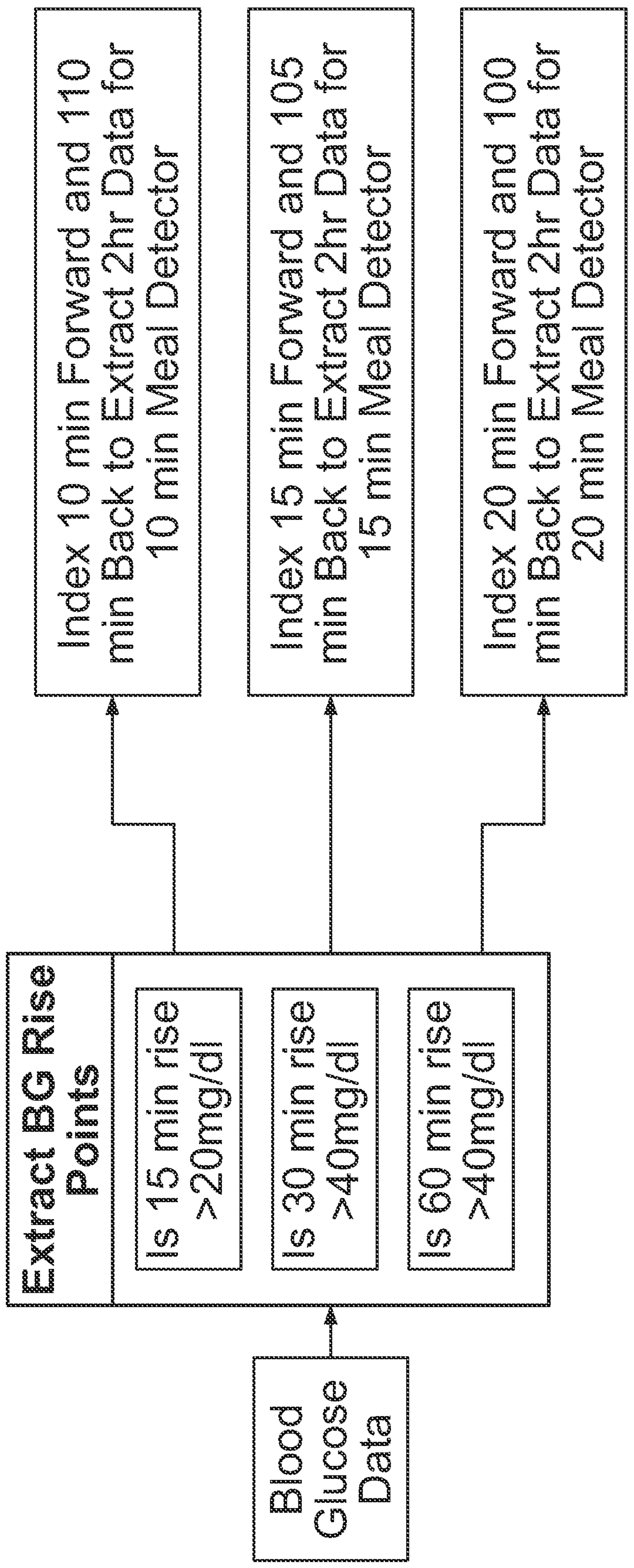
FIG. 9 is a schematic representation of the machine learning pipeline.
Figure 10:
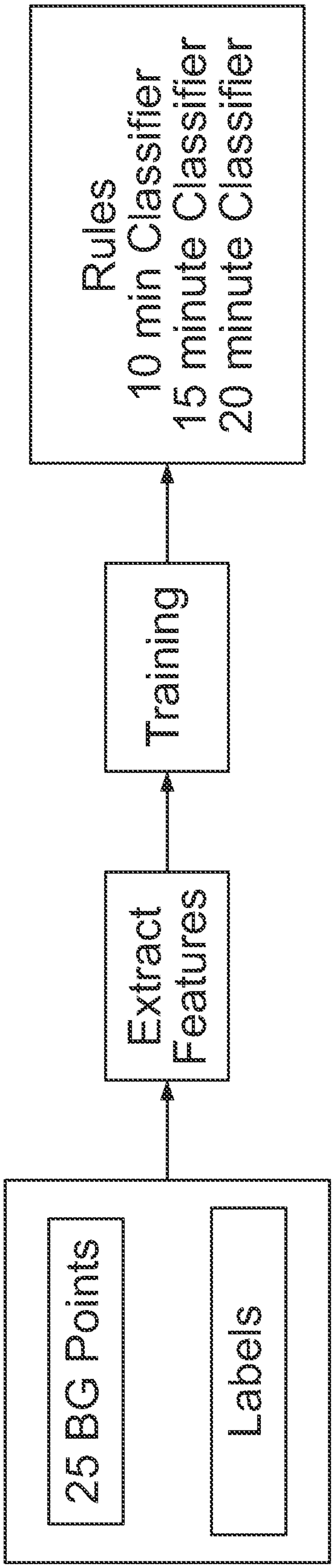
FIG. 10 shows the supervised training process for 10-minute, 15-minute and 20-minute meal detectors.

The machine learning pipeline is depicted in FIG. 9, which shows data generation for 10-minute, 15-minute and 20-minute meal detection classifiers. The BG rise points must be inside low and high thresholds. The 10-minute classifier looks forward 10 minutes and backward 110 minutes to extract 2 hours of data, the 15-minute classifier looks forward 15 minutes and backward 105 minutes to extract 2 hours of data and the 20-minute classifier looks forward 20 minutes and backward 100 minutes to extract 2 hours of data. FIG. 10 shows supervised training for the 10-minute, 15-minute and 20-minute meal classifiers.

In certain embodiments, decision trees may be used for meal detection. In one embodiment, the meals are detected using three different delay periods. These are the 10-minute delay detector, the 15-minute delay detector and the 20-minute delay detector. The 10-, 15- and 20-minute delay detectors recognize rising blood glucose values with an assumption that the post-prandial blood glucose rise started 10, 15 and 20 minutes prior to the current time, respectively. The exact rules used in the meal detection decision trees may vary based on differing embodiments of the invention. In addition, detectors using different time periods may also be developed.

Figure 11:
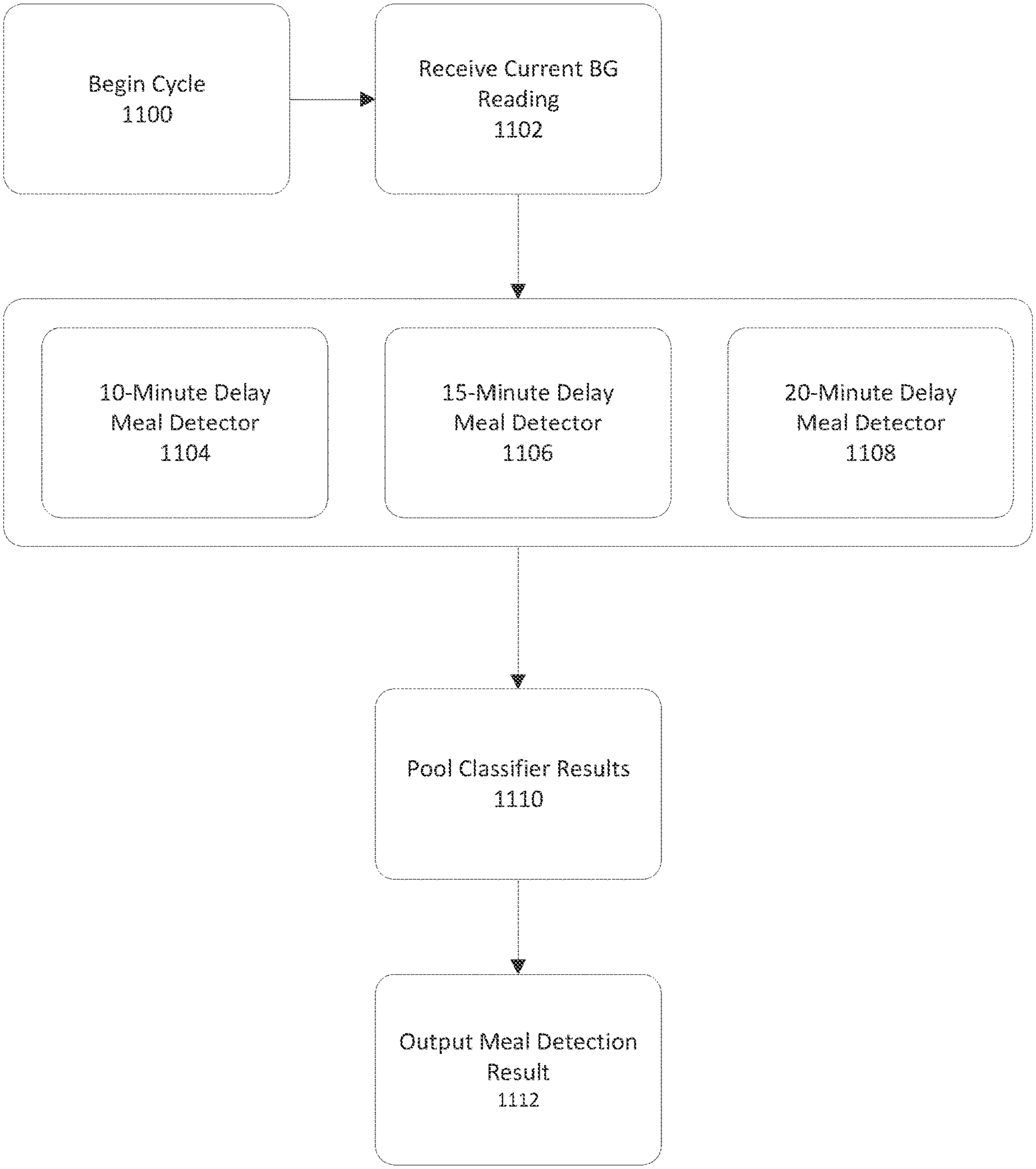
FIG. 11 is a flowchart showing the pooling of the results from the 10-, 15- and 20-minute meal detectors to provide a robust meal detection result.

Models may be cascaded and/or combined to make the meal detection more robust. At each 5 minute interval, as a new blood glucose value is received from CGM 108, the 10-, 15 and 20-minute meal detectors are fired to detect meals. These results are then synthesized, resulting in a robust meal detection model, an example of which is shown in FIG. 11. At 1100, the most recent cycle of the MDA 129 begins and, at 1102, the most recent blood glucose reading is received and added to the most recent 2-hour history. The 10-minute delay meal detector 1104, the 15-minute delay meal detector 1106 and the 20-minute delay meal detectors 1108 2-hour history of blood glucose readings. At 1110, the results from each of the delayed meal detectors 1104, 1106 and 1108 are pooled and, at 1112, the meal detection result is output. Various rules may be enforced by the pool classifier at 1110 to determine whether a meal detection is TRUE or FALSE based on the combination of results from delayed meal detectors 1104, 1106, 1108.

As an example, if, in the current cycle, the 10-minute delay meal detector returns True, it is expected that the 15-minute meal detector will return True in the next cycle (it is conceivable the 10-minute detector may return True at this cycle as well), and that, in the next cycle, the 20-minute meal detector will return True. For robustness a period of time in which these detectors may return True is allowed and the final meal detection result is synthesized by pulling the outputs of the 10-, 15-, and 20-minute detectors, as shown in FIG. 11.

Figure 12:
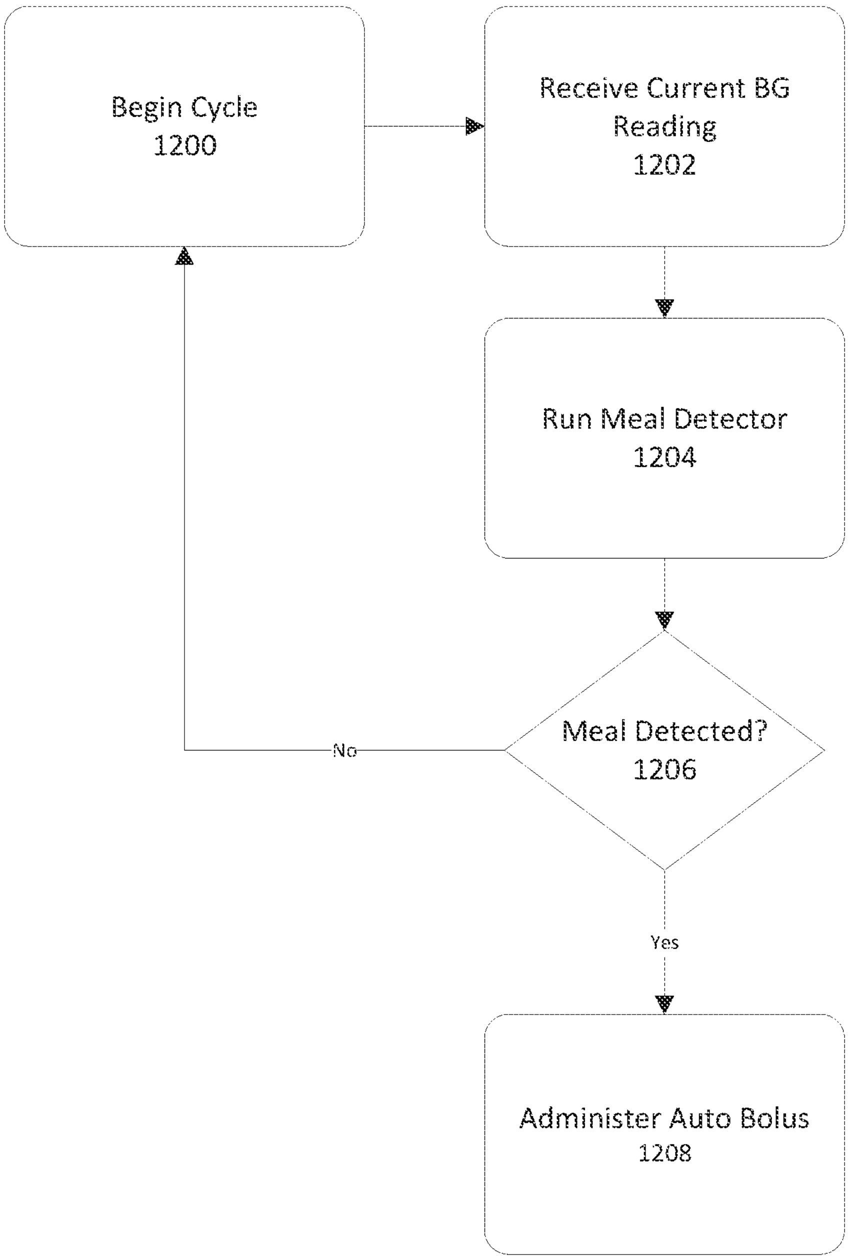
FIG. 12 is a flowchart showing the process for administering an automatic bolus of insulin.

Auto-Bolusing—In certain embodiments, when and unbolused or under-bolused meal is detected, regardless of the method used for detection, an automatic bolus dose of insulin will be fired. FIG. 12 shows the logic flow for determining whether an automatic bolus should be administered. At 1200, the cycle begins. As previously discussed, in preferred embodiments of the invention, each cycle is five minutes in length and a new blood glucose reading is received from the CGM during each five minute cycle. In certain embodiments of the invention, the receipt of a new BG reading will trigger the beginning of the next cycle. At 1202, the most recent blood glucose reading is received and, at 1204, the meal detectors previously described are run on the most recent blood glucose readings, including the most recently received reading. At 1206, if a meal has been detected, the auto bolus will be administered as described above at 1208. If no meal is detected control returns to 1200, to await the start of the next cycle.

The auto bolus may have a nominal insulin delivery volume. In one embodiment, the auto bolus may be the safe bolus dose described in detail above. In other exemplary embodiments, the insulin volume required will nominally be a percentage (e.g., 8%) of the TDI for the user. This amount of insulin will be adjusted by a safe IOB requirement ($IOB_{SR}$) for correction and modulated by the current IOB. The safe IOB requirement indicates the insulin needed for correcting the blood glucose (however, instead of using the insulin setpoint, for improved safety, an elevated value, for example, 150 mg/dl, may be used for improved safety).

$$AutoBolus = (x * TDI) + IOB_{SR} - IOB \quad (20)$$

where:

$$IOB_{SR} = \frac{(CurrentBG - 150)}{CF} \quad (21)$$

where:

CF is a correction factor defined as 1600/TDI.

In the event that a manual bolus has been administered prior to the triggering of the auto bolus, the IOB will modulate the insulin delivery. If the IOB is sufficiently high, then the auto bolus may deliver 0 units of insulin. One the other hand, if the user has under-bolused, then a suitable amount of insulin will be provided according to the IOB.

The auto bolus delivers a safe amount of insulin for post-prandial blood glucose compensation. The core closed loop control algorithm will continue to deliver the appropriate amount of basal insulin to maximize time in range for the user.

The following examples pertain to various embodiments of the systems and methods disclosed herein for providing a method for determining an optimal delivery of a drug by providing a stepwise exploration of a search space of possible quantities of the drug to be delivered to the user.

Example 1 is a method of a first embodiment of the invention comprising the steps of receiving notification of a meal event, calculating a safe bolus dose to be delivered to the user, delivering the safe bolus dose, moderating blood glucose levels of the user, and compensating for further excursions in the blood glucose levels of the user by a medication delivery algorithm of the drug delivery system.

Example 2 is an extension of Example 1, or any other example disclosed herein, wherein notification of the meal event comprises a user selection of a button in a user interface.

Example 3 is an extension of Example 1, or any other example disclosed herein, wherein the safe bolus dose is calculated as a function of a safe nominal insulin delivery amount and the current insulin on board.

Example 4 is an extension of Example 3, or any other example disclosed herein, wherein the safe nominal insulin delivery amount is calculated as a percentage of the user's total daily insulin requirement.

Example 5 is an extension of Example 4, or any other example disclosed herein, wherein the safe bolus dose is modified by a blood glucose correction factor that takes into account the current blood glucose levels of the user.

Example 6 is an extension of Example 5, or any other example disclosed herein, wherein the safe bolus dose is modified by a trend correction factor which corrects for trends in the user's blood glucose values for a past predetermined period of time.

Example 7, is an extension of Example 6, or any other example disclosed herein, wherein the trend correction factor is based on a slope and a curvature of the user's blood glucose values for the past predetermined period of time.

Example 8 is an extension of Example 5, or any other example disclosed herein, wherein when the safe bolus dose is modified by a rebound from hypo factor which reduces the safe bolus dose by a predetermined amount if the user has experienced a hypoglycemic event within a predetermined time period prior to delivery of the safe bolus dose.

Example 9 is an extension of Example 5, or any other example disclosed herein, wherein the safe bolus dose is modified by nighttime factor which reduces the safe bolus dose by calculated amount if the bolus dose is being administered during a nighttime period.

Example 10 is an extension of Example 9, or any other example disclosed herein, wherein a current value of the nighttime factor is lowered if, in past occurrences, the current value created an additional risk of hypoglycemia or is raised if, in past occurrences, the current value caused blood glucose values of the user to be elevated.

Example 11 is an extension of Example 3, or any other example disclosed herein, wherein the safe bolus dose may be modified by any combination of a blood glucose correction factor, a trend correction factor, a rebound from hypo factor and a nighttime factor.

Example 12 is an extension of Example 1, or any other example disclosed herein, wherein delivering the safe bolus dose further comprises splitting the safe bolus dose into multiple staged doses delivered at predetermined times after notification of the meal event.

Example 13 is an extension of Example 12, or any other example disclosed herein, wherein the safe bolus dose is recalculated at each staged delivery.

Example 14 is an extension of Example 1, or any other example disclosed herein, wherein the notification of a meal event comprises an automatic detection of ingestion of a meal based on blood glucose levels of the user received from a continuous glucose monitor.

Example 15 is an extension of Example 14, or any other example disclosed herein, wherein the automatic detection of the ingestion of a meal is based on detection of a significant increase in the user's blood glucose levels in a significant increase in automatic delivery of a liquid drug as calculated by a medication delivery algorithm of the drug delivery system.

Example 16 is an extension of Example 15, or any other example disclosed herein, wherein the increase in user's blood glucose levels and the increase in the automatic delivery of the liquid drug are evaluated for a moving window of a predetermined with evaluated each time a new blood glucose reading is received from the continuous blood glucose monitor.

Example 17 is an extension of Example 14, or any other example disclosed herein, wherein the automatic detection of the ingestion of a meal is based on an analysis of the plot of the user's blood glucose levels by one or more machine learning model trained is meal detection classifiers.

Example 18 is extension of Example 17, or any other example disclosed herein, wherein the one or more machine learning models are trained to detect post-prandial rises in blood glucose levels of the user beginning at various times prior to the current time Example 19 is an extension of Example 18, or any other example disclosed herein, wherein the one or more machine learning models comprise a 10-minute delay detector, 15-minute delay detector and a 20-minute delay detector.

Example 20 is an extension of Example 17, or any other example disclosed herein, wherein the one or more machine learning models are cascaded to provide a final determination of a meal ingestion.

Example 21 is an extension of Example 14, or any other example disclosed herein, wherein the automatic detection of the ingestion of a meal is based on an analysis of the plot of the user's blood glucose levels by one or more decision trees.

Example 22 is an extension of Example 21, or any other example disclosed herein, wherein the decision trees use multiple delay detectors to recognize rising blood glucose values with an assumption that a rise in the blood glucose levels started at various times prior to the current time.

Example 23 is an extension of Example 22, or any other example disclosed herein, wherein the multiple delay detectors comprise 10-, 15- and 20-minute delay detectors.

Example 24 is an extension of Example 22, or any other example disclosed herein, wherein the results of the multiple delay detectors are pooled to synthesize a final meal detection decision.

Example 25 is an extension of example 14, or any other example disclosed herein, wherein, in response to the notification of a meal event, the method further comprises informing the user of the inner unannounced detection of a meal and providing a recommended bolus dose to the user.

Example 26 is an extension of Example 25, or any other example disclosed herein, wherein, in response to the notification of the meal event, the method further comprises adjusting a medication delivery algorithm of the drug delivery system to respond more aggressively to glucose deviations based on the recommended bolus dose.

Example 27 is a method of a second embodiment of the invention comprising the steps of automatically detecting ingestion of a meal based on blood glucose levels of the user received from a continuous glucose monitor, informing the user of the unannounced detection of a meal, providing a recommended bolus dose to the user and adjusting them a medication delivery algorithm of the drug delivery system to respond more aggressively to glucose deviations based on the recommended bolus dose.

Example 28 is a system of third embodiment comprising a processor and software, executing on the processor providing the functions of receiving notification of a meal event, calculating a safe bolus dose to be delivered to the user, delivering the safe bolus dose, monitoring blood glucose levels of the user, and compensating for further excursions in the blood glucose levels of the user in accordance with the medication delivery algorithm of the drug delivery system.

Example 29 is an extension of Example 28, or any other example disclosed herein, wherein the notification of a meal event comprises a user selection of a button in the user interface of the drug delivery system.

Example 30 is an extension of Example 28, or any other example disclosed herein, further comprising a continuous glucose monitor, wherein the notification of a meal event comprises automatic detection of the ingestion of a meal based on blood glucose levels of the user received from the continuous glucose monitor.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the invention relates, many modifications and adaptations of the invention may be realized. Implementations provided herein, including values of tunable parameters, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A method of compensating for meal ingestion in a drug delivery system comprising:

automatically detecting a meal event using at least a first classifier model configured to evaluate a first sliding window of analyte values corresponding to a first duration based on a current timepoint and a second classifier model configured to evaluate a second sliding window of analyte values corresponding to a second duration based on the current timepoint that is greater than the first duration, wherein the first and second classifier models are each applied at successive analyte detector output intervals as new analyte values are received;

calculating a safe bolus dose to be delivered to a user based on the detection of the meal event;

delivering the safe bolus dose;

monitoring blood glucose levels of the user; and compensating for further excursions in the blood glucose levels of the user in accordance with a medication delivery algorithm of the drug delivery system.

2. The method of claim 1 further comprising receiving a notification of a meal event through a user selection of a button in a user interface of the drug delivery system.

3. The method of claim 1 wherein the safe bolus dose is calculated as a function of a safe nominal insulin delivery amount and the current insulin on board.

4. The method of claim 3 wherein the safe nominal insulin delivery amount is calculated as a percentage of a total daily insulin requirement (TDI) of the user.

5. The method of claim 4 wherein the safe bolus dose is modified by one or more of:

a blood glucose correction factor that takes into account the current blood glucose levels of the user;

a trend correction factor, wherein the trend correction factor corrects for trends in the user's blood glucose values for a past predetermined period of time;

a rebound from hypo factor, wherein the rebound from hypo factor reduces the safe bolus dose by a predetermined amount if the user has experienced a hypoglycemic event within a predetermined time period prior to delivery of the safe bolus dose; or a nighttime factor, wherein the nighttime factor reduces the safe bolus dose by a calculated amount if the bolus dose is being administered during a nighttime period.

6. The method of claim 5 wherein the trend correction factor is based on a slope and a curvature of the user's blood glucose values for the past predetermined period of time.

7. The method of claim 5 wherein nighttime mode is automatically detected using a motion profile provided by an IMU and time zone information.

8. The method of claim 5 wherein a current value of the nighttime factor is lowered if, in past occurrences, the current value created an additional risk of hypoglycemia or is raised if, in past occurrences, the current value caused blood glucose values of the user to be elevated.

9. The method of claim 1 wherein delivering the safe bolus dose further comprises:

splitting the safe bolus dose into multiple staged doses delivered at predetermined times after notification of the meal event.

10. The method of claim 9 wherein the safe bolus dose is recalculated at each staged delivery.

11. The method of claim 1 wherein the analyte is a blood glucose of the user and the analyte detector is a continuous glucose monitor.

12. The method of claim 11 wherein the automatic detection of the ingestion of a meal is based on detection of increase in the user's blood glucose levels by more than a predetermined threshold blood glucose value and an increase in automatic delivery of a liquid drug by more than a predetermined threshold delivery value as calculated by a medication delivery algorithm of the drug delivery system.

13. The method of claim 12 wherein the increase in the user's blood glucose levels and the increase in the automatic delivery of the liquid drug are evaluated for a moving window of a predetermined width evaluated each time a new blood glucose reading is received from the continuous glucose monitor.

14. The method of claim 11 wherein each classifier model evaluates a window of data extending both backward and forward in time relative to a current time point, wherein the total duration evaluated by each classifier model is the same across each classifier model.

15. The method of claim 14 wherein and outputs of the classifier models from a current cycle and one or more prior cycles are pooled to generate a final meal detection determination.

16. The method of claim 15, wherein the first classifier model comprises a 10-minute detector, the second classifier model comprises a 15-minute detector and further comprising a third classifier model comprising a 20-minute detector, wherein the machine learning models are cascaded to provide a final determination of a meal ingestion.

17. The method of claim 1 wherein the automatic detection of the ingestion of a meal is based on an analysis of a plot of the user's blood glucose levels by one or more decision trees that use multiple delay detectors to recognize rising blood glucose values with an assumption that a rise in the blood glucose levels started at various times prior to the current time.

18. The method of claim 17 wherein the results of the multiple delay detectors are pooled to synthesize a final meal detection decision.

19. The method of claim 1 wherein, in response to the notification of the meal event, the method further comprises:

informing the user of the unannounced detection of a meal; and providing a recommended bolus dose to the user.

20. The method of claim 19 wherein, in response to the notification of the meal event, the method further comprises:

adjusting a medication delivery algorithm of the drug delivery system to respond more aggressively to glucose deviations based on the recommended bolus dose.

* * * * *